United States Patent
Vaisvila et al.

(10) Patent No.: US 11,124,825 B2
(45) Date of Patent: **\*Sep. 21, 2021**

(54) COMPOSITIONS AND METHODS FOR ANALYZING MODIFIED NUCLEOTIDES

(71) Applicant: New England Biolabs, Inc., Ipswich, MA (US)

(72) Inventors: Romualdas Vaisvila, Ipswich, MA (US); Zhiyi Sun, Gloucester, MA (US); Shengxi Guan, Ipswich, MA (US); Lana Saleh, Hamilton, MA (US); Laurence Ettwiller, Ipswich, MA (US); Theodore B. Davis, Boxford, MA (US)

(73) Assignee: New England Biolabs, Inc., Ipswich, MA (US)

(*) Notice: Subject to any disclaimer, the term of this patent is extended or adjusted under 35 U.S.C. 154(b) by 42 days.

This patent is subject to a terminal disclaimer.

(21) Appl. No.: 16/217,819

(22) Filed: Dec. 12, 2018

(65) Prior Publication Data

US 2019/0100796 A1    Apr. 4, 2019

Related U.S. Application Data

(60) Division of application No. 15/441,431, filed on Feb. 24, 2017, now Pat. No. 10,227,646, which is a continuation-in-part of application No. PCT/US2016/059447, filed on Oct. 28, 2016.

(60) Provisional application No. 62/325,626, filed on Apr. 21, 2016, provisional application No. 62/300,396, filed on Feb. 26, 2016, provisional application No. 62/271,679, filed on Dec. 28, 2015, provisional application No. 62/257,284, filed on Nov. 19, 2015, provisional application No. 62/248,872, filed on Oct. 30, 2015.

(51) Int. Cl.
| | |
|---|---|
| *C12Q 1/6858* | (2018.01) |
| *C12Q 1/6806* | (2018.01) |
| *C12Q 1/6827* | (2018.01) |
| *C12N 9/02* | (2006.01) |
| *C12Q 1/6869* | (2018.01) |
| *C12Q 1/6872* | (2018.01) |

(52) U.S. Cl.
CPC ......... *C12Q 1/6858* (2013.01); *C12N 9/0071* (2013.01); *C12Q 1/6806* (2013.01); *C12Q 1/6827* (2013.01); *C12Q 1/6869* (2013.01); *C12Q 1/6872* (2013.01); *C12Y 114/11* (2013.01); *C12Q 2600/154* (2013.01)

(58) Field of Classification Search
CPC .. C12Q 1/6858; C12Q 1/6806; C12Q 1/6827; C12Q 1/6869; C12Q 1/6872; C12Q 2600/154; C12N 9/0071; C12Y 114/11
See application file for complete search history.

(56) References Cited

U.S. PATENT DOCUMENTS

| | | | |
|---|---|---|---|
| 9,121,061 B2 | 9/2015 | Vaisvila et al. | |
| 10,260,088 B2* | 4/2019 | Vaisvila | ............... C12Y 114/11 |
| 10,619,200 B2* | 4/2020 | Vaisvila | ............... C12Q 1/6869 |
| 2011/0183320 A1 | 7/2011 | Flushberg et al. | |
| 2013/0244237 A1 | 9/2013 | Vaisvila et al. | |
| 2018/0312914 A1* | 11/2018 | Vaisvila | ............... C12Q 1/6872 |

OTHER PUBLICATIONS

Ehrich, Nucl. Acids Res. 35:e29, 2007.
Holmes, et al. PloS one 9, No. 4: e93933, 2014.
Jin, et al., Nucleic Acids Res., 2: 6956-71, 2014.
Pais, et al, Proc. Natl. Acad. Sci. 112: 4316-4321, 2015.
Stenglein, Nature Structural & Molecular Biology 17: 222-229, 2010.
Soni, et al., Clin Chem 53: 1996-2001, 2007.
Adey, Genome Res. 24: 2041-9, 2014.
Amini, Nat Genet. 46: 1343-9, 2014.
Cabson, Nucleic Acids Res. 41:e112, 2013.
Krueger, et al. Bioinformatics 27, No. 11: 1571-1572, 2011.

* cited by examiner

*Primary Examiner* — Iqbal H Chowdhury
(74) *Attorney, Agent, or Firm* — New England Biolabs, Inc; Harriet M. Strimpel

(57) ABSTRACT

A method for identifying any of the presence, location and phasing of modified cytosines (C) in long stretches of nucleic acids is provided. In some embodiments, the method may comprise (a) reacting a first portion of a nucleic acid sample containing at least one C and/or at least one modified C with a DNA glucosyltransferase and a cytidine deaminase to produce a first product and/or reacting a second portion of the sample with a dioxygenase, optionally a DNA glucosyltransferase and a cytidine deaminase to produce a second product and; (b) comparing the sequences from the first and optionally the second product obtained in (a), or amplification products thereof, with each other and/or an untreated reference sequence to determine which Cs in the initial nucleic acid fragment are modified. A modified TET methylcytosine dioxygenase with improved efficiency compared to unmodified TET2 at converting methylcytosine to carboxymethylcytosine is also provided.

7 Claims, 20 Drawing Sheets
(8 of 20 Drawing Sheet(s) Filed in Color)
Specification includes a Sequence Listing.

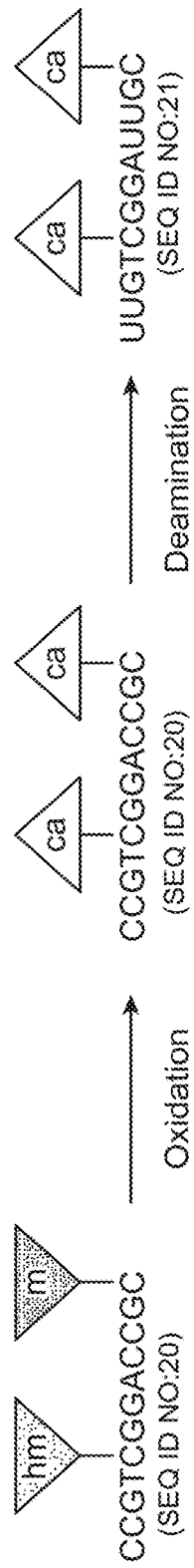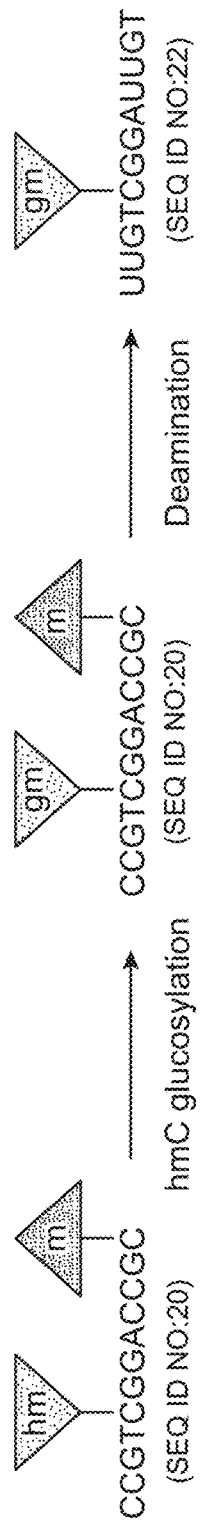

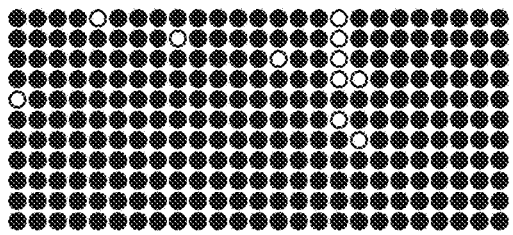 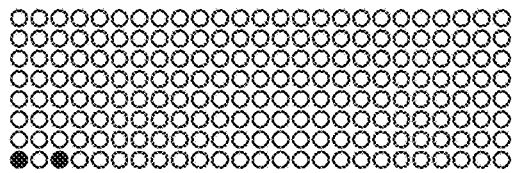
FIG. 2A  FIG. 2B
| Genomic DNA | DNA % methylation (dmC/dC) | DNA % hydroxymethylation (dhmC/dmC) |
|---|---|---|
| Mouse fibroblast NHI/3T3 gDNA | 3.21 | 0.2 |
FIG. 2C

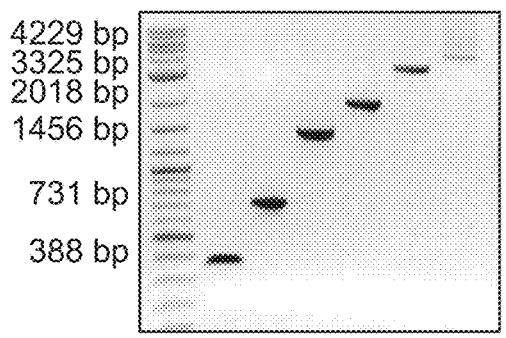
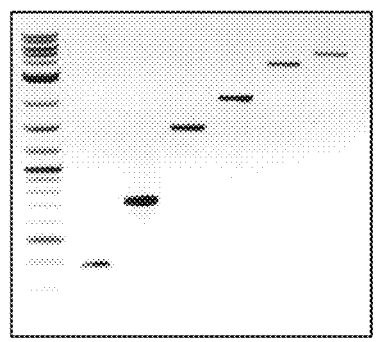
FIG. 3A  FIG. 3B
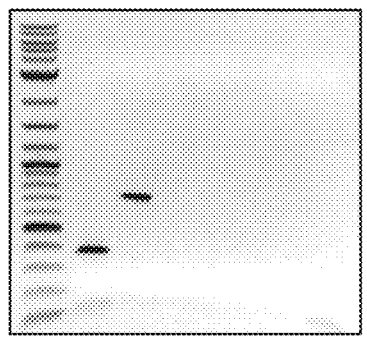
FIG. 3C
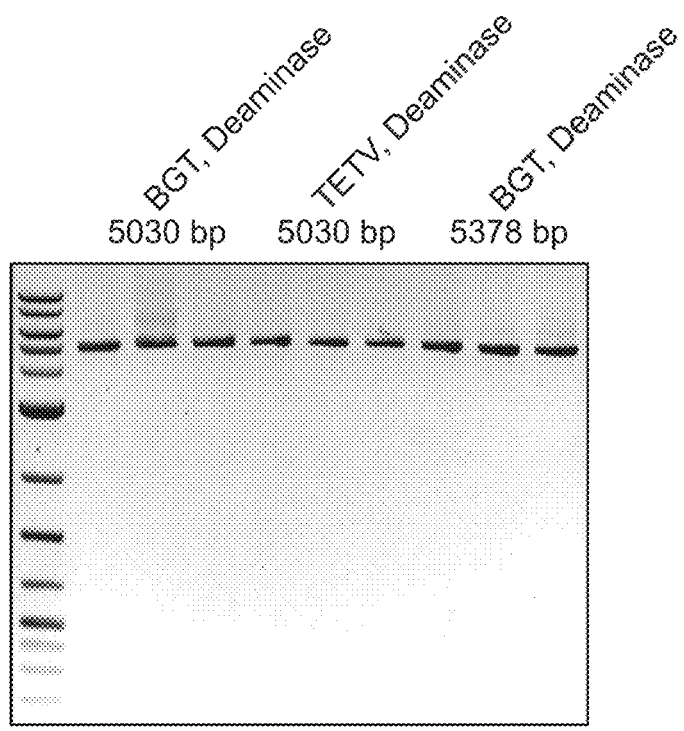
FIG. 3D

| Library | Starting Material | Replicate | Reads (million) | C conversion rate |
|---|---|---|---|---|
| APOBEC-seq | Mouse E14 50ng | 1 | 127 | 99.9% |
| APOBEC-seq | 50ng | 2 | 124 | 99.9% |
| APOBEC-seq | 1ng | 1 | 165 | 99.8% |
| APOBEC-seq | 1ng | 2 | 145 | 99.8% |

SEQUENCE LISTING

<160> NUMBER OF SEQ ID NOS: 22

<210> SEQ ID NO 1
<211> LENGTH: 507

```
<212> TYPE: PRT
<213> ORGANISM: Artificial Sequence
<220> FEATURE:
<223> OTHER INFORMATION: Synthetic construct

<400> SEQUENCE: 1

Gly Gly Ser Gln Ser Gln Asn Gly Lys Cys Glu Gly Cys Asn Pro Asp
1               5                   10                  15

Lys Asp Glu Ala Pro Tyr Tyr Thr His Leu Gly Ala Gly Pro Asp Val
            20                  25                  30

Ala Ala Ile Arg Thr Leu Met Glu Glu Arg Tyr Gly Glu Lys Gly Lys
        35                  40                  45

Ala Ile Arg Ile Glu Lys Val Ile Tyr Thr Gly Lys Glu Gly Lys Ser
    50                  55                  60

Ser Gln Gly Cys Pro Ile Ala Lys Trp Val Tyr Arg Arg Ser Ser Glu
65                  70                  75                  80

Glu Glu Lys Leu Leu Cys Leu Val Arg Val Arg Pro Asn His Thr Cys
                85                  90                  95

Glu Thr Ala Val Met Val Ile Ala Ile Met Leu Trp Asp Gly Ile Pro
            100                 105                 110

Lys Leu Leu Ala Ser Glu Leu Tyr Ser Glu Leu Thr Asp Ile Leu Gly
        115                 120                 125

Lys Cys Gly Ile Cys Thr Asn Arg Arg Cys Ser Gln Asn Glu Thr Arg
    130                 135                 140

Asn Cys Cys Cys Gln Gly Glu Asn Pro Glu Thr Cys Gly Ala Ser Phe
145                 150                 155                 160

Ser Phe Gly Cys Ser Trp Ser Met Tyr Tyr Asn Gly Cys Lys Phe Ala
                165                 170                 175

Arg Ser Lys Lys Pro Arg Lys Phe Arg Leu His Gly Ala Glu Pro Lys
            180                 185                 190

Glu Glu Glu Arg Leu Gly Ser His Leu Gln Asn Leu Ala Thr Val Ile
        195                 200                 205

Ala Pro Ile Tyr Lys Lys Leu Ala Pro Asp Ala Tyr Asn Asn Gln Val
    210                 215                 220

Glu Phe Glu His Gln Ala Pro Asp Cys Cys Leu Gly Leu Lys Glu Gly
225                 230                 235                 240

Arg Pro Phe Ser Gly Val Thr Ala Cys Leu Asp Phe Ser Ala His Ser
                245                 250                 255

His Arg Asp Gln Gln Asn Met Pro Asn Gly Ser Thr Val Val Val Thr
            260                 265                 270

Leu Asn Arg Glu Asp Asn Arg Glu Val Gly Ala Lys Pro Glu Asp Glu
        275                 280                 285

Gln Phe His Val Leu Pro Met Tyr Ile Ile Ala Pro Glu Asp Glu Phe
    290                 295                 300

Gly Ser Thr Glu Gly Gln Glu Lys Lys Ile Arg Met Gly Ser Ile Glu
305                 310                 315                 320

Val Leu Gln Ser Phe Arg Arg Arg Val Ile Arg Ile Gly Glu Leu
                325                 330                 335

Pro Lys Ser Cys Glu Val Ser Gly Gln Asp Ala Ala Val Gln Glu
            340                 345                 350

Ile Glu Tyr Trp Ser Asp Ser Glu His Asn Phe Gln Asp Pro Cys Ile
        355                 360                 365

Gly Gly Val Ala Ile Ala Pro Thr His Gly Ser Ile Leu Ile Glu Cys
    370                 375                 380
```

```
Ala Lys Cys Glu Val His Ala Thr Thr Lys Val Asn Asp Pro Asp Arg
385                 390                 395                 400

Asn His Pro Thr Arg Ile Ser Leu Val Leu Tyr Arg His Lys Asn Leu
            405                 410                 415

Phe Leu Pro Lys His Cys Leu Ala Leu Trp Glu Ala Lys Met Ala Glu
        420                 425                 430

Lys Ala Arg Lys Glu Glu Cys Gly Lys Asn Gly Ser Asp His Val
            435                 440                 445

Ser Gln Lys Asn His Gly Lys Gln Glu Lys Arg Glu Pro Thr Gly Pro
    450                 455                 460

Gln Glu Pro Ser Tyr Leu Arg Phe Ile Gln Ser Leu Ala Glu Asn Thr
465                 470                 475                 480

Gly Ser Val Thr Thr Asp Ser Thr Val Thr Thr Ser Pro Tyr Ala Phe
                485                 490                 495

Thr Gln Val Thr Gly Pro Tyr Asn Thr Phe Val
                500                 505

<210> SEQ ID NO 2
<211> LENGTH: 11
<212> TYPE: PRT
<213> ORGANISM: Artificial Sequence
<220> FEATURE:
<223> OTHER INFORMATION: Synthetic construct

<400> SEQUENCE: 2

Glu Leu Pro Lys Ser Cys Glu Val Ser Gly Gln
1               5                   10

<210> SEQ ID NO 3
<211> LENGTH: 871
<212> TYPE: PRT
<213> ORGANISM: Artificial Sequence
<220> FEATURE:
<223> OTHER INFORMATION: Synthetic construct

<400> SEQUENCE: 3

Gln Ser Gln Asn Gly Lys Cys Glu Gly Cys Asn Pro Asp Lys Asp Glu
1               5                   10                  15

Ala Pro Tyr Tyr Thr His Leu Gly Ala Gly Pro Asp Val Ala Ala Ile
            20                  25                  30

Arg Thr Leu Met Glu Glu Arg Tyr Gly Glu Lys Gly Lys Ala Ile Arg
        35                  40                  45

Ile Glu Lys Val Ile Tyr Thr Gly Lys Glu Gly Lys Ser Ser Gln Gly
    50                  55                  60

Cys Pro Ile Ala Lys Trp Val Tyr Arg Arg Ser Ser Glu Glu Glu Lys
65              70                  75                  80

Leu Leu Cys Leu Val Arg Val Arg Pro Asn His Thr Cys Glu Thr Ala
                85                  90                  95

Val Met Val Ile Ala Ile Met Leu Trp Asp Gly Ile Pro Lys Leu Leu
            100                 105                 110

Ala Ser Glu Leu Tyr Ser Glu Leu Thr Asp Ile Leu Gly Lys Cys Gly
        115                 120                 125

Ile Cys Thr Asn Arg Arg Cys Ser Gln Asn Glu Thr Arg Asn Cys Cys
    130                 135                 140

Cys Gln Gly Glu Asn Pro Glu Thr Cys Gly Ala Ser Phe Ser Phe Gly
145                 150                 155                 160

Cys Ser Trp Ser Met Tyr Tyr Asn Gly Cys Lys Phe Ala Arg Ser Lys
                165                 170                 175
```

```
Lys Pro Arg Lys Phe Arg Leu His Gly Ala Glu Pro Lys Glu Glu
            180                 185                 190

Arg Leu Gly Ser His Leu Gln Asn Leu Ala Thr Val Ile Ala Pro Ile
        195                 200                 205

Tyr Lys Lys Leu Ala Pro Asp Ala Tyr Asn Asn Gln Val Glu Phe Glu
210                 215                 220

His Gln Ala Pro Asp Cys Cys Leu Gly Leu Lys Glu Gly Arg Pro Phe
225                 230                 235                 240

Ser Gly Val Thr Ala Cys Leu Asp Phe Ser Ala His Ser His Arg Asp
                245                 250                 255

Gln Gln Asn Met Pro Asn Gly Ser Thr Val Val Thr Leu Asn Arg
            260                 265                 270

Glu Asp Asn Arg Glu Val Gly Ala Lys Pro Glu Asp Glu Gln Phe His
        275                 280                 285

Val Leu Pro Met Tyr Ile Ile Ala Pro Glu Asp Glu Phe Gly Ser Thr
290                 295                 300

Glu Gly Gln Glu Lys Lys Ile Arg Met Gly Ser Ile Glu Val Leu Gln
305                 310                 315                 320

Ser Phe Arg Arg Arg Val Ile Arg Ile Gly Glu Leu Pro Lys Ser
            325                 330                 335

Cys Lys Lys Lys Ala Glu Pro Lys Lys Ala Lys Thr Lys Lys Ala Ala
        340                 345                 350

Arg Lys Arg Ser Ser Leu Glu Asn Cys Ser Ser Arg Thr Glu Lys Gly
            355                 360                 365

Lys Ser Ser His Thr Lys Leu Met Glu Asn Ala Ser His Met Lys
            370                 375                 380

Gln Met Thr Ala Gln Pro Gln Leu Ser Gly Pro Val Ile Arg Gln Pro
385                 390                 395                 400

Pro Thr Leu Gln Arg His Leu Gln Gln Gly Gln Arg Pro Gln Pro
            405                 410                 415

Gln Pro Pro Gln Pro Gln Pro Gln Thr Thr Pro Gln Pro Gln Pro Gln
                420                 425                 430

Pro Gln His Ile Met Pro Gly Asn Ser Gln Ser Val Gly Ser His Cys
            435                 440                 445

Ser Gly Ser Thr Ser Val Tyr Thr Arg Gln Pro Thr Pro His Ser Pro
    450                 455                 460

Tyr Pro Ser Ser Ala His Thr Ser Asp Ile Tyr Gly Asp Thr Asn His
465                 470                 475                 480

Val Asn Phe Tyr Pro Thr Ser Ser His Ala Ser Gly Ser Tyr Leu Asn
                485                 490                 495

Pro Ser Asn Tyr Met Asn Pro Tyr Leu Gly Leu Leu Asn Gln Asn Asn
            500                 505                 510

Gln Tyr Ala Pro Phe Pro Tyr Asn Gly Ser Val Pro Val Asp Asn Gly
        515                 520                 525

Ser Pro Phe Leu Gly Ser Tyr Ser Pro Gln Ala Gln Ser Arg Asp Leu
    530                 535                 540

His Arg Tyr Pro Asn Gln Asp His Leu Thr Asn Gln Asn Leu Pro Pro
545                 550                 555                 560

Ile His Thr Leu His Gln Gln Thr Phe Gly Asp Ser Pro Ser Lys Tyr
                565                 570                 575

Leu Ser Tyr Gly Asn Gln Asn Met Gln Arg Asp Ala Phe Thr Thr Asn
            580                 585                 590
```

-continued

```
Ser Thr Leu Lys Pro Asn Val His Leu Ala Thr Phe Ser Pro Tyr
            595                 600                 605

Pro Thr Pro Lys Met Asp Ser His Phe Met Gly Ala Ala Ser Arg Ser
610                 615                 620

Pro Tyr Ser His Pro His Thr Asp Tyr Lys Thr Ser Glu His His Leu
625                 630                 635                 640

Pro Ser His Thr Ile Tyr Ser Tyr Thr Ala Ala Ala Ser Gly Ser Ser
                645                 650                 655

Ser Ser His Ala Phe His Asn Lys Glu Asn Asp Asn Ile Ala Asn Gly
            660                 665                 670

Leu Ser Arg Val Leu Pro Gly Phe Asn His Asp Arg Thr Ala Ser Ala
        675                 680                 685

Gln Glu Leu Leu Tyr Ser Leu Thr Gly Ser Ser Gln Glu Lys Gln Pro
690                 695                 700

Glu Val Ser Gly Gln Asp Ala Ala Ala Val Gln Glu Ile Glu Tyr Trp
705                 710                 715                 720

Ser Asp Ser Glu His Asn Phe Gln Asp Pro Cys Ile Gly Gly Val Ala
                725                 730                 735

Ile Ala Pro Thr His Gly Ser Ile Leu Ile Glu Cys Ala Lys Cys Glu
            740                 745                 750

Val His Ala Thr Thr Lys Val Asn Asp Pro Asp Arg Asn His Pro Thr
        755                 760                 765

Arg Ile Ser Leu Val Leu Tyr Arg His Lys Asn Leu Phe Leu Pro Lys
770                 775                 780

His Cys Leu Ala Leu Trp Glu Ala Lys Met Ala Glu Lys Ala Arg Lys
785                 790                 795                 800

Glu Glu Glu Cys Gly Lys Asn Gly Ser Asp His Val Ser Gln Lys Asn
                805                 810                 815

His Gly Lys Gln Glu Lys Arg Glu Pro Thr Gly Pro Gln Glu Pro Ser
            820                 825                 830

Tyr Leu Arg Phe Ile Gln Ser Leu Ala Glu Asn Thr Gly Ser Val Thr
        835                 840                 845

Thr Asp Ser Thr Val Thr Thr Ser Pro Tyr Ala Phe Thr Gln Val Thr
850                 855                 860

Gly Pro Tyr Asn Thr Phe Val
865                 870

<210> SEQ ID NO 4
<211> LENGTH: 44
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (18)..(18)
<223> OTHER INFORMATION: n is Pyrrolo-dC

<400> SEQUENCE: 4
ataagaatag aatgaatngt gaaatgaata tgaaatgaat agta            44

<210> SEQ ID NO 5
<211> LENGTH: 65
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
```

```
<222> LOCATION: (4)..(4)
<223> OTHER INFORMATION: n is Pyrrolo-dc
<220> FEATURE:
<221> NAME/KEY: misc_feature
<222> LOCATION: (12)..(12)
<223> OTHER INFORMATION: n is Pyrrolo-dc
<220> FEATURE:
<221> NAME/KEY: misc_feature
<222> LOCATION: (14)..(14)
<223> OTHER INFORMATION: n is Pyrrolo-dc
<220> FEATURE:
<221> NAME/KEY: misc_feature
<222> LOCATION: (16)..(16)
<223> OTHER INFORMATION: n is Pyrrolo-dc
<220> FEATURE:
<221> NAME/KEY: misc_feature
<222> LOCATION: (19)..(19)
<223> OTHER INFORMATION: n is Pyrrolo-dc
<220> FEATURE:
<221> NAME/KEY: misc_feature
<222> LOCATION: (24)..(24)
<223> OTHER INFORMATION: n is Pyrrolo-dc
<220> FEATURE:
<221> NAME/KEY: misc_feature
<222> LOCATION: (26)..(27)
<223> OTHER INFORMATION: n is Pyrrolo-dc
<220> FEATURE:
<221> NAME/KEY: misc_feature
<222> LOCATION: (31)..(31)
<223> OTHER INFORMATION: n is Pyrrolo-dc
<220> FEATURE:
<221> NAME/KEY: misc_feature
<222> LOCATION: (34)..(34)
<223> OTHER INFORMATION: n is Pyrrolo-dc
<220> FEATURE:
<221> NAME/KEY: misc_feature
<222> LOCATION: (36)..(36)
<223> OTHER INFORMATION: n is Pyrrolo-dc
<220> FEATURE:
<221> NAME/KEY: misc_feature
<222> LOCATION: (38)..(38)
<223> OTHER INFORMATION: n is Pyrrolo-dc
<220> FEATURE:
<221> NAME/KEY: misc_feature
<222> LOCATION: (42)..(44)
<223> OTHER INFORMATION: n is Pyrrolo-dc
<220> FEATURE:
<221> NAME/KEY: misc_feature
<222> LOCATION: (47)..(47)
<223> OTHER INFORMATION: n is Pyrrolo-dc
<220> FEATURE:
<221> NAME/KEY: misc_feature
<222> LOCATION: (49)..(49)
<223> OTHER INFORMATION: n is Pyrrolo-dc
<220> FEATURE:
<221> NAME/KEY: misc_feature
<222> LOCATION: (52)..(52)
<223> OTHER INFORMATION: n is Pyrrolo-dc
<220> FEATURE:
<221> NAME/KEY: misc_feature
<222> LOCATION: (54)..(54)
<223> OTHER INFORMATION: n is Pyrrolo-dc
<220> FEATURE:
<221> NAME/KEY: misc_feature
<222> LOCATION: (56)..(56)
<223> OTHER INFORMATION: n is Pyrrolo-dc
<220> FEATURE:
<221> NAME/KEY: misc_feature
<222> LOCATION: (59)..(60)
<223> OTHER INFORMATION: n is Pyrrolo-dc

<400> SEQUENCE: 5
gatnggaaga gnanangtnt gaantnnagt nuanantntt tnnntanang angntnttnn      60
gatct                                                                 65

<210> SEQ ID NO 6
```

```
<211> LENGTH: 25
<212> TYPE: DNA
<213> ORGANISM: Artificial Sequence
<220> FEATURE:
<223> OTHER INFORMATION: Synthetic construct

<400> SEQUENCE: 6
aatgaaggaa atgaatttgg tagag                                          25

<210> SEQ ID NO 7
<211> LENGTH: 25
<212> TYPE: DNA
<213> ORGANISM: Artificial Sequence
<220> FEATURE:
<223> OTHER INFORMATION: Synthetic construct

<400> SEQUENCE: 7
tcccaaatac ataaatccac actta                                          25

<210> SEQ ID NO 8
<211> LENGTH: 34
<212> TYPE: DNA
<213> ORGANISM: Artificial Sequence
<220> FEATURE:
<223> OTHER INFORMATION: Synthetic construct

<400> SEQUENCE: 8
taggataaaa atataaatgt attgtgggat gagg                                34

<210> SEQ ID NO 9
<211> LENGTH: 27
<212> TYPE: DNA
<213> ORGANISM: Artificial Sequence
<220> FEATURE:
<223> OTHER INFORMATION: Synthetic construct

<400> SEQUENCE: 9
aaaacatata acccctcca ctaatac                                         27

<210> SEQ ID NO 10
<211> LENGTH: 31
<212> TYPE: DNA
<213> ORGANISM: Artificial Sequence
<220> FEATURE:
<223> OTHER INFORMATION: Synthetic construct

<400> SEQUENCE: 10
agatatattg gagaagtttt ggatgatttg g                                   31

<210> SEQ ID NO 11
<211> LENGTH: 27
<212> TYPE: DNA
<213> ORGANISM: Artificial Sequence
<220> FEATURE:
<223> OTHER INFORMATION: Synthetic construct

<400> SEQUENCE: 11
aaaacatata acccctcca ctaatac                                         27

<210> SEQ ID NO 12
<211> LENGTH: 25
<212> TYPE: DNA
<213> ORGANISM: Artificial Sequence
<220> FEATURE:
<223> OTHER INFORMATION: Synthetic construct

<400> SEQUENCE: 12
```
taagattaag gtaggttgga tttgg                                              25

<210> SEQ ID NO 13
<211> LENGTH: 25
<212> TYPE: DNA
<213> ORGANISM: Artificial Sequence
<220> FEATURE:
<223> OTHER INFORMATION: Synthetic construct

<400> SEQUENCE: 13
tcattactcc ctctccaaaa attac                                              25

<210> SEQ ID NO 14
<211> LENGTH: 25
<212> TYPE: DNA
<213> ORGANISM: Artificial Sequence
<220> FEATURE:
<223> OTHER INFORMATION: Synthetic constuct

<400> SEQUENCE: 14
aagatttaag ggaaggttga atagg                                              25

<210> SEQ ID NO 15
<211> LENGTH: 25
<212> TYPE: DNA
<213> ORGANISM: Artificial Sequence
<220> FEATURE:
<223> OTHER INFORMATION: Synthetic construct

<400> SEQUENCE: 15
acctacaaaa ccttacaaac ataac                                              25

<210> SEQ ID NO 16
<211> LENGTH: 30
<212> TYPE: DNA
<213> ORGANISM: Artificial Sequence
<220> FEATURE:
<223> OTHER INFORMATION: Synthetic construct

<400> SEQUENCE: 16
tggagtttgt tgggggttt gttgtttaag                                          30

<210> SEQ ID NO 17
<211> LENGTH: 30
<212> TYPE: DNA
<213> ORGANISM: Artificial Sequence
<220> FEATURE:
<223> OTHER INFORMATION: Synthetic construct

<400> SEQUENCE: 17
tctaaccctc accaccttcc taatacccaa                                         30

<210> SEQ ID NO 18
<211> LENGTH: 30
<212> TYPE: DNA
<213> ORGANISM: Artificial Sequence
<220> FEATURE:
<223> OTHER INFORMATION: Synthetic construct

<400> SEQUENCE: 18
tggtaaaggt taagaaggga agattgtgga                                         30

<210> SEQ ID NO 19
<211> LENGTH: 30
<212> TYPE: DNA

```
<213> ORGANISM: Artificial Sequence
<220> FEATURE:
<223> OTHER INFORMATION: Synthetic construct

<400> SEQUENCE: 19
aaccctactt ccccctaaca aattttcaac                                          30

<210> SEQ ID NO 20
<211> LENGTH: 12
<212> TYPE: DNA
<213> ORGANISM: Artificial Sequence
<220> FEATURE:
<223> OTHER INFORMATION: Synthetic construct

<400> SEQUENCE: 20
ccgtcggacc gc                                                             12

<210> SEQ ID NO 21
<211> LENGTH: 12
<212> TYPE: DNA
<213> ORGANISM: Artificial Sequence
<220> FEATURE:
<223> OTHER INFORMATION: Synthetic construct

<400> SEQUENCE: 21
uugtcggauu gc                                                             12

<210> SEQ ID NO 22
<211> LENGTH: 12
<212> TYPE: DNA
<213> ORGANISM: Artificial Sequence
<220> FEATURE:
<223> OTHER INFORMATION: Synthetic construct

<400> SEQUENCE: 22
uugtcggauu gt                                                             12
```

COMPOSITIONS AND METHODS FOR ANALYZING MODIFIED NUCLEOTIDES

CROSS REFERENCE

This application is a divisional of U.S. application Ser. No. 15/441,431 filed Feb. 24, 2017 which is a continuation-in-part of International Application No. PCT/US16/59447 filed Oct. 28, 2016 which claims the benefit of U.S. Provisional Application Nos.: 62/248,872, filed Oct. 30, 2015, 62/257,284, filed Nov. 19, 2015 and 62/271,679, filed Dec. 28, 2015, which applications are incorporated by reference herein.

BACKGROUND

The ability to phase modified nucleotides (e.g., methylated or hydroxymethylated nucleotides) in a genome (i.e., determine whether two or more modified nucleotides are linked on the same single DNA molecule or on different DNA molecules) can provide important information in epigenetic studies, particularly for studies on imprinting, gene regulation, and cancer. In addition, it would be useful to know which modified nucleotides are linked to sequence variations.

Modified nucleotides cannot be phased using conventional methods for investigating DNA modification because such methods typically involve bisulfite sequencing (BS-seq). In BS-seq methods, a DNA sample is treated with sodium bisulfite, which converts cytosines (C) to uracil (U), but methylcytosine ($^{m}$C) remains unchanged. When bisulfite-treated DNA is sequenced, unmethylated C is read as thymine (T), and $^{m}$C is read as C, yielding single-nucleotide resolution information about the methylation status of a segment of DNA. However, sodium bisulfite is known to fragment DNA (see, e.g., Ehrich M 2007 Nucl. Acids Res. 35:e29), making it impossible to determine whether modified nucleotides are linked on the same DNA molecule. Specifically, it is impossible for nucleotide modifications to be phased in the same way that sequence variants (e.g., polymorphisms) are phased because those methods require intact, long molecules.

Moreover, bisulfite sequencing displays a bias toward cytosine (C) adjacent to certain nucleotides and not others. It would be desirable to remove the observed bias.

SUMMARY

Provided herein are methods for phasing modified nucleotides that do not require bisulfite treatment. Further, such methods can be implemented in a way that distinguishes between $^{m}$C and hydroxymethylcytosine ($^{hm}$C) or C, formylcytosine ($^{f}$C) and carboxylcytosine ($^{ca}$C), providing significant advantages over conventional methods.

This disclosure provides, among other things, compositions and methods to detect and phase methylation and/or hydroxymethylation of nucleotides or unmodified nucleotides in cis or trans at a single molecule level in long stretches of DNA. In various embodiments, glucosylation and oxidation reactions overcome the observed inherent deamination of $^{hm}$C and $^{m}$C by deaminases. Deaminases converts $^{m}$C to T and C to U while glucosylhydroxymethylcytosine ($^{ghm}$C) and $^{ca}$C are not deaminated. Examples of deaminases include APOBEC (apolipoprotein B mRNA editing enzyme, catalytic polypeptide-like). Embodiments utilize enzymes that have substantially no sequence bias in glycosylation, oxidation and deamination of cytosine. Moreover, embodiments provide substantially no non-specific damage of the DNA during the glycosylation, oxidation and deamination reactions.

In some embodiments, a DNA glucosyltransferase (GT) for example beta glucosyltransferase (BGT) is utilized for glucosylating $^{hm}$C to protect this modified base from deamination. However, a person of ordinary skill in the art will appreciate that other enzymatic or chemical reactions may be used for modifying the $^{hm}$C to achieve the same effect. One alternative example provided herein is the use of Pyrrolo-dC for protecting cytosine from being converted to uracil by cytidine deaminase.

In general, in one aspect, methods for detecting nucleic acid (NA) methylation are provided that include subjecting the NA to enzymatic glucosylation, enzymatic oxidation and enzymatic deamination where an unmodified C is converted to a U, $^{m}$C is converted to T, an $^{hm}$C that is glucosylated ($^{ghm}$C) and remains C and a modified C that is oxidized to $^{ca}$C remain C. The majority of modified C are predicted to be $^{f}$C. For some diagnostic purposes, differentiating between $^{m}$C and $^{hm}$C is not required. Accordingly, it is sufficient to utilize a single pathway of oxidation and glucosylation followed by deamination. Where it is desirable to distinguish $^{m}$C from $^{hm}$C, this can be achieved by a performing two different reactions on two aliquots of the same sample and subsequently comparing the sequences of the DNA obtained. One reaction utilizes a GT and a cytidine deaminase while a second reaction utilizes a methylcytosine dioxygenase and a cytidine deaminase. It has been found here that the presence of GT in a reaction with a methylcytosine deoxygenase results in an outcome which shows an improved conversion rate (greater than 97%, 98% or 99% conversion, preferably at least 99%) of modified bases and more accurate mapping than would otherwise be possible. Methylcytosine dioxygenase variants are described herein which catalyze the conversion of the $^{m}$C to $^{hm}$C to $^{f}$C and then $^{ca}$C with little or no bias caused by neighboring nucleotides. These and other improved properties of such variants are also described herein. Methods using enzymes described herein utilizing phasing or other sequencing methods are more time and sample efficient and provide improved accuracy for diagnostic sequencing of $^{m}$C and other modified nucleotides.

In each of these methods, it is desirable to compare the product of the enzyme reactions with each other and/or an unreacted sequence. Comparing sequences can be achieved by hybridization techniques and/or by sequencing. Prior to comparing sequences, it may be desirable to amplify the NA using PCR or isothermal methods and/or clone the reacted sequence.

The NA fragments being analyzed may be DNA, RNA or a hybrid or chimera of DNA and RNA. The NA fragments may be single stranded (ss) or double stranded (ds). The NA fragments may be genomic DNA or synthetic DNA.

The size of the fragments may be any size but for embodiments of the present invention that utilize single molecule sequencing, fragment sizes that are particularly advantageous are greater than 1 Kb, 2 Kb, 3 kb, 4 kb, 5 kb, 6 Kb, 7 Kb or larger (for example, preferably greater than 4 kb) with no theoretical limitation on the upper size although the upper size of the fragment may be limited by the polymerase in the amplification step commonly used prior to sequencing if amplification is needed.

In some cases, the sequences obtained from the reactions are compared with a corresponding reference sequence to determine: (i) which Cs are converted into a U in the first product for differentiating a $^{m}$c from a $^{hm}$C; and (ii) which Cs are converted to a U for differentiating an unmodified C from a modified C in the optional second product. In these embodiments, the reference sequence may be a hypothetical deaminated sequence, a hypothetical deaminated and PCR amplified sequence or a hypothetical non-deaminated sequence for example.

In any embodiment, the first and second products may be amplified prior to sequencing. In these embodiments, any U's in the first and second products may be read as T's in the resultant sequence reads.

In any embodiment, the methylcytosine dioxygenase may convert $^mC$ and $^{hm}C$ to $^{ca}C$ so that cytidine deaminase cannot deaminate $^mC$ or $^{hm}C$. The methylcytosine dioxygenase may be a TET protein that enzymatically converts modified Cs to $^{ca}C$.

In any embodiment, the GT may be a DNA 3-glucosyl-transferase (βGT) or α-glucosyltransferase (αGT) that forms $^{ghm}C$ so that substantially no $^{hm}C$ is deaminated by the cytidine deaminase.

In any embodiment, the NA sample may contain at least one CpG island. In another embodiment, the NA may include at least two modified Cs with nucleotide neighbors selected from CpG, CpA, CpT and CpC.

In any embodiment, the method may comprise determining the location of the $^mC$ and/or $^{hm}C$ on a ss of the NA where the NA is ds.

In any embodiment, the NA is a fragment of genomic DNA and, in some cases, the NA may be linked to a transcribed gene (e.g., within 50 kb, within 20 kb, within 10 kb, within 5 kb or within 1 kb) of a transcribed gene.

The method summarized above may be employed in a variety of applications. A method for sample analysis is provided. In some embodiments, this method may comprise one or more of the following steps: (a) determining the location of all modified Cs in a test NA fragment to identify a pattern for the modified C; (b) comparing the pattern of C modifications in the test NA fragment with the pattern of C modifications in a reference NA; (c) identifying a difference in the pattern of cytosine modifications in the test NA fragment relative to the reference NA fragment; and (d) determining a pattern of $^{hm}C$ in the test NA fragment.

In some embodiments, this method may comprise comparing the pattern of C modification or unmodified C for a NA fragment that is linked, in cis, to a gene in a transcriptionally active state to the pattern of C modifications in the same intact NA fragment that is linked, in cis, to the same gene in a transcriptionally inactive state. In these embodiments, the level of transcription of the gene may be correlated with a disease or condition.

In some embodiments, this method may comprise comparing the pattern of cytosine modification for a NA fragment from a patient that has a disease or condition with the pattern of C modification in the same NA fragment from a patient that does not have the disease or condition. In other embodiments, the method may comprise comparing the pattern of cytosine modification for a NA fragment from a patient is undergoing a treatment with the pattern of C modification in the same intact NA fragment from a patient that has not been treated with the agent. In another embodiment, detected differences in the pattern of C modification in the test NA fragment relative to the reference NA fragment corresponds to a variant single nucleotide polymorphism, an insertion/deletion or a somatic mutation associated with a pathology.

A variety of compositions are also provided. In some embodiments, the composition may comprise a NA, wherein the NA comprises: a) G, A, T, U, C; b) G, A, T, U, $^{ca}C$ and no C and/or C) G, A, T, U and $^{ghm}C$ and no C and/or G, A, T, U, $^{ca}C$ and $^{ghm}C$ and no C. In some embodiments, the composition may further comprise a cytidine deaminase or mutant thereof (as described in U.S. Pat. No. 9,121,061), or a methylcytosine dioxygenase or mutant thereof as described below.

A kit is also provided. In some embodiments, the kit may comprise a GT, a methylcytosine dioxygenase e.g., a mutant methylcytosine dioxygenase (TETv as described below) and a cytidine deaminase, as well as instructions for use. As would be apparent, the various components of the kit may be in separate vessels.

In general, in one aspect, a protein is described that includes an amino acid sequence that is at least 90% identical to SEQ ID NO:1; and contains SEQ ID NO:2. In one aspect, the protein is a fusion protein that includes an N-terminal affinity binding domain. The protein may have methylcytosine dioxygenase activity where the methylcytosine deoxygenase activity is similarly effective for NCA, NCT, NCG and NCC in a target DNA. The protein may be employed in any method herein.

In any embodiment, the protein may be a fusion protein. In these embodiments, the variant protein may comprise an N-terminal affinity binding domain.

Also provided by this disclosure is a method for modifying a naturally occurring DNA containing one or more methylated C. In some embodiments, this method may comprise combining a sample comprising the DNA with a variant methylcytosine dioxygenase to make a reaction mix; and incubating the reaction mix to oxidize the methylated cytosine in the DNA.

In some embodiments, the reaction mix may further comprising analyzing the oxidized sample, e.g., by sequencing or mass spectrometry.

In some embodiments, the reaction mix may further comprise a GT.

In some embodiments, the method may be done in vitro, in a cell-free reaction.

In some embodiments, the method may be done in vitro, e.g., in cultured cells.

The above-summarized variant methylcytosine dioxygenase can be used as a methylcytosine dioxygenase in any of the methods, compositions or kits described below.

In general in one aspect, a method is provided for determining the location of modified cytosines in a nucleic acid fragment, that includes: (a) reacting a nucleic acid sample containing at least one C and/or at least one modified C with a methylcytosine dioxygenase and a DNA glucosyltransferase in a single buffer either together or sequentially; (b) reacting the product of (a) with a cytidine deaminase; and (c) comparing the sequences obtained in (a), or amplification products thereof, with an untreated reference sequence to determine which Cs in the initial nucleic acid fragment are modified. In one aspect, the methylcytosine dioxygenase is an amino acid sequence that is at least 90% identical to SEQ ID NO:1; and contains the amino acid sequence of SEQ ID NO:2.

BRIEF DESCRIPTION OF THE FIGURES

The patent or application file contains at least one drawing executed in color. Copies of this patent or patent application publication with color drawings will be provided by the office upon request and payment of the necessary fee.

Certain aspects of the following detailed description are best understood when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures:

FIG. 1A shows a schematic diagram of a method for protecting modified Cs from deamination by a cytidine deaminase and a $^mC$ dioxygenase, for example a TET enzyme such as TETv, that converts $^mC$ and $^{hm}C$ (not C) to $^{ca}C$ that are insensitive to deamination. After methylcytosine dioxygenase treatment, deamination of unmodified C only occurs resulting in its replacement by U. From left to right: SEQ ID NO.:20, SEQ ID NO. 20, SEQ ID NO. 21.

FIG. 1B shows a second method for protecting $^{hm}C$ but not $^mC$ from deamination by APOBEC enzyme. Here $^{hm}C$ is glucosylated using a βGT for example T4-βGT or αGT for example T4-αGT. C and $^mC$ are modified by a cytidine deaminase (e.g. deaminase) to a U and a T respectively. From left to right: SEQ ID NO:20, SEQ ID NO:20, SEQ ID NO:22.

FIG. 1C is a table showing readouts of bases of a genomic sample after PCR amplification and Sanger sequencing or NGS sequencing.

FIG. 2A-2B shows the methylation and hydroxymethylation status of mouse genomic DNA.

FIG. 2A shows the distribution of $^mC$ and $^{hm}C$ at a single locus (locus size: 1078 bp) of mouse fibroblast NHI/3T3 genomic DNA following methylcytosine dioxygenase (here TETv) and cytidine deaminase treatment (according to FIG. 1A).

FIG. 2B shows the distribution of $^{hm}C$ at the same locus as FIG. 3A after GT (here βGT) and cytidine deaminase treatment (according to FIG. 1B).

FIG. 2C is a summary of LC-MS data of methylation status of a locus in genomic DNAs of mouse fibroblasts.

FIG. 3A-3E shows that ss DNA is not damaged during preparation and analysis using TETv and/or βGT and cytidine deaminase in contrast to methods that use conventional bisulfite treatment (for bisulfite method see for example, Holmes, et al. *PloS one* 9, no. 4 (2014): e93933).

FIG. 3A shows results obtained with βGT and cytidine deaminase. Six different fragment sizes (388 bp, 731 bp, 1456 bp, 2018 bp, 3325 bp, and 4229 bp) were analyzed after treatment with a cytidine deaminase and βGT. Full length fragments in each size category were amplified. No fragmentation was observed.

FIG. 3B shows results obtained with TETv and cytidine deaminase. 6 different fragment sizes (388 bp, 731 bp, 1456 bp, 2018 bp, 3325 bp, and 4229 bp) were analyzed after treatment with a cytidine deaminase and βGT. Full length fragments in each size category were amplified. No fragmentation was observed.

FIG. 3C shows results obtained with bisulfite converted DNA. 6 different fragment sizes (388 bp, 731 bp, 1456 bp, 2018 bp, 3325 bp, and 4229 bp) were analyzed after bisulfite treatment. Full length fragments in each size category were amplified. When bisulfite converted DNA was amplified, only the two smallest fragments were obtained because of the breakdown of the larger fragments by the bisulfite method.

FIG. 3D shows results obtained with the primers for 5030 bp amplicon, and 5378 bp amplicon after treating DNA before amplification with T4-βGT ($^{hm}C$ detection) or TETv ($^mC+^{hm}C$ detection), and cytidine deaminase (see FIGS. 1A and 1B). Each amplification is shown in triplicate. No fragmentation was observed.

FIG. 3E shows that a 15 kb fragment of ss DNA containing $^mC/^{hm}C$ is not damaged during preparation and analysis using TETv/βGT/cytidine deaminase enzymes in contrast to methods that use conventional bisulfite treatment. The light blue line represents the denatured ss DNA of the 15 kb fragment which is also the control. The red line is APOBEC deamination on glucosylated DNA. The dark blue is DNA deamination on TETv oxidized DNA. And the green is bisulfite treated DNA.

FIG. 4A shows the results of treating oligonucleotide (5'-ATAAGAATAGAATGAATXGTGAAATGAA TATGAAATGAATAGTA-3', X=Pyrrolo-dC, SEQ ID NO:4) with cytidine deaminase at 37° C. for 16 hours (upper line (black)). The control (lower line (grey)) is untreated SEQ ID NO:4. No difference was observed between the sample and the control confirming that cytidine deaminase does not deaminate Pyrrolo-dC.

FIG. 4B shows a chromatogram (LC-MS) of an adaptor containing Pyrrolo dC, with the following sequence, where X=Pyrrolo-dC.5'/5Phos/GATXGGAAGAGXAXAXGTXT-GAAXTXXAGTX/deoxyU/AXAAXTXTTTXXXTAX-AXGAXGXTXTTXXGATCT (SEQ ID NO:5). The LC-MS chromatogram confirms that all C's are replaced by Pyrrolo-dC, with no trace of contaminated Cs.

FIG. 6A shows a pie chart of wild type lambda genome as a control with the naturally occurring distribution of CT, CA, CG and CC.

FIG. 6B shows the representation of $^mC$ in a lambda genome where every C has been methylated using Deaminase-seq. The observed distribution matches that found in FIG. 6A.

FIG. 6C shows the representation of $^mC$ in a lambda genome where every C has been methylated using BS-seq (Qiagen). The observed distribution is not consistent with that found in FIG. 6A.

FIG. 6D shows the representation of $^mC$ in a lambda genome where every C has been methylated using BS-seq (Zymo). The observed distribution is not consistent with that found in FIG. 6A.

FIG. 8A shows the distribution of reads for DNA Deaminase-seq.

FIG. 8B shows the distribution of reads for BS-seq (Qiagen).

FIG. 8C shows the distribution of reads for BS-seq (Zymo).

FIG. 11A shows that the present method can be used to phase $^mC$ (red=methylated; blue=unmethylated).

FIG. 11B shows that the present method can be used to phase $^{hm}C$ (red=hydroxymethylated and blue=unmodified).

FIG. 12B shows activity of TETv on ss and ds genomic (3T3) DNA is similar.

DEFINITIONS

Figure 3E:
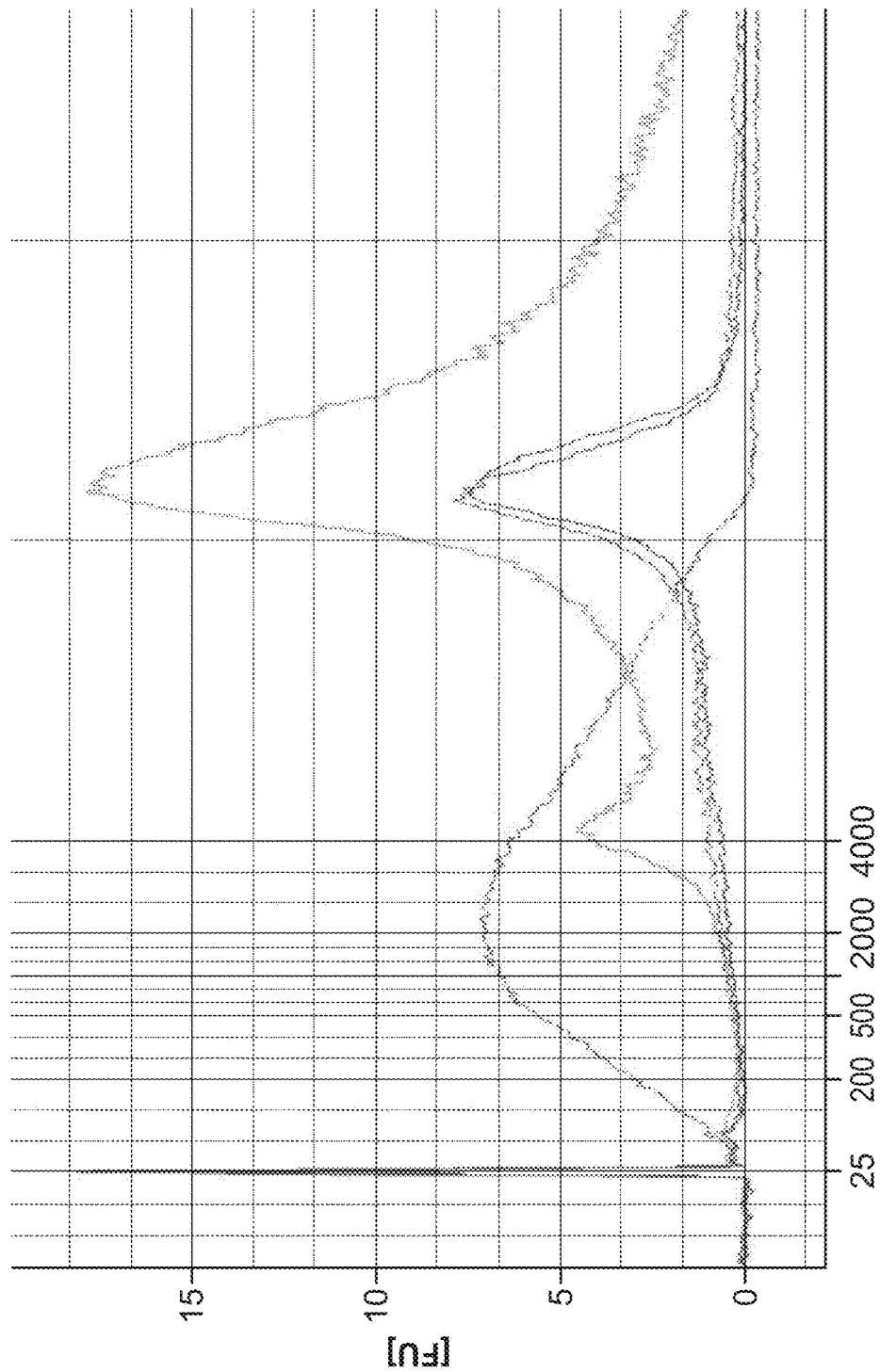

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

As used herein, the term "buffering agent", refers to an agent that allows a solution to resist changes in pH when acid or alkali is added to the solution. Examples of suitable non-naturally occurring buffering agents that may be used in the compositions, kits, and methods of the invention include, for example, Tris, HEPES, TAPS, MOPS, tricine, or MES.

The term "non-naturally occurring" refers to a composition that does not exist in nature.

Any protein described herein may be non-naturally occurring, where the term "non-naturally occurring" refers to a protein that has an amino acid sequence and/or a post-translational modification pattern that is different to the protein in its natural state. For example, a non-naturally occurring protein may have one or more amino acid substitutions, deletions or insertions at the N-terminus, the C-terminus and/or between the N- and C-termini of the protein. A "non-naturally occurring" protein may have an amino acid sequence that is different to a naturally occurring amino acid sequence (i.e., having less than 100% sequence identity to the amino acid sequence of a naturally occurring protein) but that is at least 80%, at least 85%, at least 90%, at least 95%, at least 97%, at least 98% or at least 99% identical to the naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell. A "mutant" protein may have one or more amino acid substitutions relative to a wild-type protein and a "fusion" protein may have one or exogenous domains added to the N-terminus, C-terminus, and or the middle portion of the protein.

In the context of a nucleic acid (NA), the term "non-naturally occurring" refers to a NA that contains: a) a sequence of nucleotides that is different to a NA in its natural state (i.e. having less than 100% sequence identity to a naturally occurring NA sequence), b) one or more non-naturally occurring nucleotide monomers (which may result in a non-natural backbone or sugar that is not G, A, T or C) and/or C) may contain one or more other modifications (e.g., an added label or other moiety) to the 5'-end, the 3' end, and/or between the 5'- and 3'-ends of the NA.

In the context of a composition, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

As used herein, the term "composition" refers to a combination of reagents that may contain other reagents, e.g., glycerol, salt, dNTPs, etc., in addition to those listed. A composition may be in any form, e.g., aqueous or lyophilized, and may be at any state (e.g., frozen or in liquid form).

As used herein, the term "location" refers to the position of a nucleotide in an identified strand in a NA molecule.

As used herein, the term "phasing" refers to a determination of the status of two or more nucleotides on a single DNA molecule or within an allele (i.e. whether the nucleotides are modified or not, for example, whether the nucleotides such as C are methylated, hydroxymethylated, formyl modified or carboxylated or unmodified) are on the same molecule of NA or different homologous chromosomes from a single cell or from homologous chromosomes from different cells in a sample noting that in different cells or different tissues, homologous chromosomes may have a different epigenetic status.

As used herein, the term "nucleic acid" (NA) refers to a DNA, RNA, DNA/RNA chimera or hybrid that may be ss or ds and may be genomic or derived from the genome of a eukaryotic or prokaryotic cell, or synthetic, cloned, amplified, or reverse transcribed. In certain embodiments of the methods and compositions, NA preferably refers to genomic DNA as the context requires.

As used herein, the term "modified cytosine" refers to methylcytosine ($^m$C), hydroxymethylcytosine ($^{hm}$C), formyl modified, carboxy modified or modified by any other chemical group that may be found naturally associated with C.

As used herein, the term "methylcytosine dioxygenase" refers to an enzyme that converts $^m$C to $^{hm}$C. TET1 (Jin, et al., Nucleic Acids Res. 2014 42: 6956-71) is an example of a methylcytosine dioxygenase, although many others are known including TET2, TET3 and Naeglaria TET (Pais et al, Proc. Natl. Acad. Sci. 2015 112: 4316-4321). Examples of methylcytosine dioxygenases which may be referred to as "oxygenase" are provided in U.S. Pat. No. 9,121,061. TETv is an example of a methylcytosine dioxygenase that oxidizes at least 90%, 92%, 94%, 96%, or 98% of all modified C.

As used herein, the term "cytidine deaminase" refers to an enzyme that is capable of deaminating C to form a U. Many cytidine deaminases are known. For example, the APOBEC family of cytidine deaminases is described in U.S. Pat. No. 9,121,061. APOBEC 3A (Stenglein, Nature Structural & Molecular Biology 2010 17: 222-229) is an example of a deaminase. In any embodiment, the deaminase used may have an amino acid sequence that is at least 90% identical to (e.g., at least 95% identical to) the amino acid sequence of GenBank accession number AKE33285.1, which is the human APOBEC3A. Preferably, the cytidine deaminase converts unmodified cytosine to uracil with an efficiency of at least 90%, 92%, 94%, 96%, 98% preferably at least 96%.

As used herein, the term "DNA glucosyltransferase (GT)" refers to an enzyme that catalyzes the transfer of a β or α-D-glucosyl residue UDP-glucose to $^{hm}$C residue in DNA. An example of a GT is T4-βGT. In one example, the use of GT follows a deoxygenase reaction and ensures that deamination of $^{hm}$C is blocked so that less than 10% or 7% or 5% or 3% (preferably less than 3% of $^{hm}$C) is converted to U by the deaminase.

The term "substantially" refers to greater than 50%, 60%, 70%, 80%, or more particularly 90% of the whole.

As used herein, the term "comparing" refers to analyzing two or more sequences relative to one another. In some cases, comparing may be done by aligning or more sequences with one another such that correspondingly positioned nucleotides are aligned with one another.

As used herein, the term "reference sequence" refers to the sequence of a fragment that is being analyzed. A reference sequence may be obtained from a public database or it may be separately sequenced as part of an experiment. In some cases, the reference sequence may be "hypothetical" in the sense that it may be computationally deaminated (i.e., to change C's into U's or T's etc.) to allow a sequence comparison to be made.

As used herein, the terms "G", "A", "T", "U", "C", "$^m$C", "$^{ca}$C", "$^{hm}$C" and "$^{ghm}$C" refer to nucleotides that contain guanidine (G), adenine (A), thymine (T), uracil (U), cytosine (C), $^m$C, $^{ca}$C, $^{hm}$C and $^{ghm}$C, respectively. For clarity, C, $^{ca}$C, $^m$C and $^{ghm}$C are different moieties.

As used herein, the term "no C", in the context of a NA fragment that contains no C, refers to a NA fragment that contains no C. Such a NA may contain $^{ca}$C, $^m$C and/or $^{ghm}$C and other nucleotides other than C.

The term "internal" refers to a location within the polypeptide that is within a region that extends up to 20 amino acids from either end of the polypeptide.

The term "repeat" refers to a plurality of amino acids that are repeated within the polypeptide.

The term "fusion" refers to a protein having one or exogenous binding domains added to the N-terminus, C-terminus, and or the middle portion of the protein. The binding domain is capable of recognizing and binding to another molecule. Thus, in some embodiments the binding domain is a histidine tag ("His-tag"), a maltose-binding protein, a chitin-binding domain, a SNAP-tag® (New England Biolabs, Ipswich, Mass.) or a DNA-binding domain, which may include a zinc finger and/or a transcription activator-like (TAL) effector domain.

As used herein "N-terminal portion of the protein" refers to amino acids within the first 50% of the protein. As used herein "C-terminal portion of the protein refers to the terminal 50% of the protein.

The term "Next Generation Sequencing (NGS)" generally applies to sequencing libraries of genomic fragments of a size of less than 1 kb preferably using an Illumina sequencing platform. In contrast, single molecule sequencing is performed using a platform from Pacific Biosystems, Oxford Nanopore, or 10× Genomics or any other platform known in the art that is capable of sequencing molecules of length greater than 1 kb or 2 kb.

DETAILED DESCRIPTION OF THE EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Almost all studies on C modification in eukaryotic genomes have ignored the fact that eukaryotic genomes carry two or more copies of each chromosome. Thus, most traditional studies on C modification do not provide any information about linkage between modified C. For example, methylation studies have traditionally been done using sodium bisulfite, which converts C into U. However, as shown below, sodium bisulfite also fragments DNA, thereby making it difficult, if not impossible, to determine whether two nearby modified C, are linked on the same DNA molecules or unlinked on different molecules. The method described herein provides a solution to this problem.

In some embodiments, the sequencing may be done in a way that allows one to determine the identity and location of unmodified or modified C, as well as whether those unmodified or modified C that are linked on the same molecule (i.e., "phased"). For example, in some embodiments, the method may comprise reacting a first portion of a sample that contains relatively long, intact NA fragments (e.g., at least 1 kb, at least 5 kb, at least 10 kb, at least 50 kb, up to 100 kb or 200 kb or more in length) with a GT and a cytidine deaminase to produce a first product. This product differentiates C and $^{m}$C from $^{hm}$C as shown in FIG. 1B. A second portion of the sample may be reacted with a methylcytosine dioxygenase (and optionally a GT) as shown in FIG. 1A. The methylcytosine dioxygenase and the GT may be combined in the same reaction mix or used sequentially in the same or different buffers. This reaction is followed by a cytidine deaminase reaction to distinguish between unmodified C and modified C. Depending on the sequence of the initial fragment (e.g., whether the initial fragment in FIG. 1B contains G, A, T, C, $^{m}$C and, in some cases, $^{hm}$C), the first product may contain G, A, T, U, no C and $^{ghm}$C (if the initial fragment contained $^{hm}$C). In FIG. 1A, the second product alone may contain G, A, T, U, $^{ca}$C and no C. These enzyme and methods avoid degradation of the NA substrate and provide improved phasing of modified nucleotide over long pieces of the genome that are not degraded by the enzymes. These enzyme and methods achieve sequencing and mapping of modified nucleotides with minimal bias and improved efficiency.

After the first and optionally second products are produced, they may be amplified and/or cloned, and then sequenced using suitable sequencing method. This may include single molecule sequencing for phased sequencing, Phased sequencing may be done in a variety of different ways. In some embodiments, the products may be sequenced using a long read single-molecule sequencing approach such as Nanopore sequencing (e.g. as described in Soni, et al Clin Chem 53: 1996-2001 2007, and developed by Oxford Nanopore Technologies) or Pacific Biosciences' fluorescent base-cleavage method (which currently have an average read length of over 10 kb, with some reads over 60 kb). Alternatively, the products may be sequenced using, the methods of Moleculo (lllumina, San Diego, Calif.), 10× Genomics (Pleasanton, Calif.), or NanoString Technologies (Seattle, Wash.). In these methods, the sample is optionally diluted and then partitioned into a number of partitions (wells of a microtitre plate or droplets in an emulsion, etc.) in an amount that limits the probability that each partition does not contain two molecules of the same locus (e.g., two molecules containing the same gene). Next, these methods involve producing indexed amplicons of a size that is compatible with the sequencing platform being used (e.g., amplicons in the range of 200 bp to 1 kb in length) where amplicons derived from the same partitions are barcoded with the same index unique to the partition. Finally, the indexed amplicons are sequenced, and the sequence of the original, long, molecules can be reconstituted using the index sequences. Phased sequencing may also be done using barcoded transposons (see, e.g., Adey Genome Res. 2014 24: 2041-9 and Amini Nat Genet. 2014 46: 1343-9), and by using the "reflex" system of Population Genetics Technologies (Casbon, Nucleic Acids Res. 2013 41:e112).

Alternatively, the genome may be fragmented into fragments of less than 1 kb in size to form a library for Next gen sequencing. Pyrrolo-dC modified adaptors may be added to the fragments in the library prior to enzyme treatment according to FIGS. 1A-1B and Example 1. After the enzyme reaction, the adaptor ligated libraries may be sequenced using an Illumina sequencer. After the sequences of the first and optionally the second product are obtained, the sequences are compared with a reference sequence to determine which C's in the initial NA fragment are modified. A matrix illustrating an embodiment of this part of the method is illustrated in FIG. 1C. In some embodiments, this comparing may be done by comparing the sequences obtained from the first product of the sample (i.e., the methylcytosine dioxygenase (and optionally GT) and cytidine deaminase treated portion of the sample) and the untreated sample and/or second product of the sample (i.e., the GT and cytidine deaminase treated portion of the sample) with a corresponding reference sequence (untreated and/or the first product). Possible outcomes include:

i. The position of a C in the initial NA fragment is identified by a U in both the first and second products;

ii. The position of a $^mC$ in the initial NA fragment is determined by the presence of a C in the first product or a T in the second product iii. The position of a $^{hm}C$ in the initial NA fragment is determined by the presence of a C in the second product only.

It should be noted that should there be no need to differentiate the $^mC$ from the rarer $^{hm}C$, then this information can be obtained from the second product only (FIG. 1A).

As would be understood, if the product is cloned, amplified or sequenced by a polymerase, a "U" will be read as "T". In these embodiments, nucleotides read as a T in both the first and second products still indicate Cs that have been changed to Us in the initial deamination reaction.

As would be recognized, some of the analysis steps of the method, e.g., the comparing step, can be implemented on a computer. In certain embodiments, a general-purpose computer can be configured to a functional arrangement for the methods and programs disclosed herein. The hardware architecture of such a computer is well known by a person skilled in the art, and can comprise hardware components including one or more processors (CPU), a random-access memory (RAM), a read-only memory (ROM), an internal or external data storage medium (e.g., hard disk drive). A computer system can also comprise one or more graphic boards for processing and outputting graphical information to display means. The above components can be suitably interconnected via a bus inside the computer. The computer can further comprise suitable interfaces for communicating with general-purpose external components such as a monitor, keyboard, mouse, network, etc. In some embodiments, the computer can be capable of parallel processing or can be part of a network configured for parallel or distributive computing to increase the processing power for the present methods and programs. In some embodiments, the program code read out from the storage medium can be written into memory provided in an expanded board inserted in the computer, or an expanded unit connected to the computer, and a CPU or the like provided in the expanded board or expanded unit can actually perform a part or all of the operations according to the instructions of the program code, so as to accomplish the functions described below. In other embodiments, the method can be performed using a cloud computing system. In these embodiments, the data files and the programming can be exported to a cloud computer that runs the program and returns an output to the user.

A system can, in certain embodiments, comprise a computer that includes: a) a central processing unit; b) a main non-volatile storage drive, which can include one or more hard drives, for storing software and data, where the storage drive is controlled by disk controller; c) a system memory, e.g., high speed random-access memory (RAM), for storing system control programs, data, and application programs, including programs and data loaded from non-volatile storage drive; system memory can also include read-only memory (ROM); d) a user interface, including one or more input or output devices, such as a mouse, a keypad, and a display; e) an optional network interface card for connecting to any wired or wireless communication network, e.g., a printer; and f) an internal bus for interconnecting the aforementioned elements of the system.

The method described above can be employed to analyze genomic DNA from virtually any organism, including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the genomic DNA used in the method may be derived from a mammal, where in certain embodiments the mammal is a human. In exemplary embodiments, the genomic sample may contain genomic DNA from a mammalian cell, such as, a human, mouse, rat, or monkey cell. The sample may be made from cultured cells, formalin fixed samples or cells of a clinical sample, e.g., a tissue biopsy (for example from a cancer), scrape or lavage or cells of a forensic sample (i.e., cells of a sample collected at a crime scene). In particular embodiments, the NA sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, and semen. In particular embodiments, a sample may be obtained from a subject, e.g., a human. In some embodiments, the sample analyzed may be a sample of cell-free DNA obtained from blood, e.g., from the blood of a pregnant female.

In some embodiments of the invention, an enzymatic method has been provided which permits the sequencing of short and long NA (for example, ss DNA and ds DNA) to discover modified bases and to determine the phasing of such bases in the genome. Embodiments of the method may include a composition comprising a mixture of one or two enzymes where the one, two enzymes are selected from a methylcytosine dioxygenase and a GT where the cytidine deaminase is added in a subsequent reaction. The dioxygenase and GT may be stored in the same or different buffers and combined as desired in a storage buffer or in a reaction mixture. When added separately to a reaction mixture, the addition may be sequential or the enzymes may be added together at the start of the reaction. Embodiments of the method may utilize two or more enzymes selected from a cytidine deaminase, a methylcytosine dioxygenase and a GT. Embodiments of the method may include a methylcytosine dioxygenase and a cytidine deaminase used sequentially in a reaction mixture; a methylcytosine dioxygenase and a GT used sequentially or together preferably followed by a deaminase reaction; or a methylcytosine dioxygenase, GT and cytidine deaminase used sequentially or together.

In some embodiments, that utilize a GT, a UDP may be added to the reaction mixture.

In one embodiment, the methylcytosine dioxygenase and optionally the GT may be added to ds DNA in an initial step and then removed by a proteinase treatment, heat treatment and/or separation treatment. This may be followed by a cytidine deaminase reaction with separation and isolation of the deaminated DNA. In some embodiments, the pH of the cytidine deaminase reaction mixture is in the range of pH 5.5-8.5, for example pH 6.0-8.0 for example, pH 6.0, pH 6.3, pH 6.5, pH 6.8, pH 7.0, pH 7.5, or pH 8.0 wherein the specific activity of the cytidine deaminase is increased at the lower end of the pH range such as at pH 6.0.

In one embodiment, concentration ranges of enzymes utilized in the reaction described for 1 µg DNA include: 0.001-100 micrograms of a methylcytosine dioxygenase such as the Ngo TET (Pais, supra), TET1, TET2 or TET3 or mutants thereof; 0.001-100 micrograms cytidine deaminase such as APOBEC or Deaminase; 0.001-100 units GT such as T4-βGT or T4-αGT. When Pyrollo-dC used in adaptor synthesis, a standard procedure described in Example 4 is followed. The amount of UDP used follows the recommendation of the manufacturer.

The ss DNA product of enzyme reaction or reactions can be amplified by PCR or isothermal method such ligase mediated amplification (LMA), helicase dependent amplification (HDA), rolling circle amplification (RCA), loop mediated amplification (LAMP), multiple displacement amplification, (MDA); transcription mediated amplification (TMA), strand displacement amplification (SDA), nicking enzyme amplification reaction (NEAR).

The amplified or indeed non-amplified DNA may be sequenced using any of the sequencing platforms in development or commercially available such as provided by Illumina, Oxford Nanopore, or Pacific Biosystems, or methods in development or commercially available such as Sanger sequencing or any WGS (whole genome sequencing) method. Long reads are mapped to the genome using the appropriate algorithm, for example, Bismark (see for example, Krueger et al. *Bioinformatics* 27, no. 11 (2011): 1571-1572). The methylation status is called when each reads is mapped to the targeted region (for example, enhancer and promoter region).

Present embodiments provide many advantages over existing systems that result from factors that include: a lower error rate in identifying mC regardless of adjacent nucleotides, and a lower error rate in detecting low level methylations; no systematic sequence preference; more consistent genome wide sequencing coverage; higher coverage in C rich regions and CpG islands; covering more CpG sites where these may be distributed widely in the genome portion being analyzed; and accurate detection of $^{hm}C$ of large fragments (5 kb) at a base resolution enabling phasing of DNA modifications and phasing DNA modifications together with other genomic features such as SNPs or variants.

In some embodiments, the composition may comprise a NA that is made up of nucleotides G, A, T, U, $^{ca}C$, wherein the NA contains substantially no C. In some embodiments, the composition may comprise a NA that is made up of nucleotides G, A, T, U and $^{ghm}C$, wherein the NA contains substantially no C. In either embodiment, the composition may also contain a cytidine deaminase (e.g., a cytidine deaminase that is at least 90% identical to an APOBEC cytidine deaminase) and, in certain embodiments, may also contain a buffering agent and other components (e.g., NaCl) in amounts that are compatible with cytidine deaminase activity. The composition may be an aqueous composition.

Variant, $^{m}C$ Dioxygenases and Methods for Using the Same

A variant methylcytosine dioxygenase is also provided. In some embodiments, the methylcytosine dioxygenase comprises an amino acid sequence that is at least 90% identical to (e.g., at least 92%, at least 94%, at least 96%, at least 97%, at least 98%, or at least 99% identical to) the amino acid sequence of TETv (SEQ ID NO:1); and contain the amino acid sequence of SEQ ID NO:2. As would be apparent, this polypeptide has $^{m}C$ dioxygenase activity. The TETv sequence is shown below:

```
TETv
                                  (SEQ ID NO: 1)
GGSQSQNGKCEGCNPDKDEAPYYTHLGAGPDVAAIRTLMEERYGEKGKAI

RIEKVIYTGKEGKSSQGCPIAKWVYRRSSEEEKLLCLVRVRPNHTCETAV

MVIAIMLWDGIPKLLASELYSELTDILGKCGICTNRRCSQNETRNCCCQG

ENPETCGASFSFGCSWSMYYNGCKFARSKKPRKFRLHGAEPKEEERLGSH

LQNLATVIAPIYKKLAPDAYNNQVEFEHQAPDCCLGLKEGRPFSGVTACL
```

```
                            -continued
DFSAHSHRDQQNMPNGSTVVVTLNREDNREVGAKPEDEQFHVLPMYIIAP

EDEFGSTEGQEKKIRMGSIEVLQSFRRRRVIRIG*ELPKSCEVSGQ*DAAA

VQEIEYWSDSEHNFQDPCIGGVAIAPTHGSILIECAKCEVHATTKVNDPD

RNHPTRISLVLYRHKNLFLPKHCLALWEAKMAEKARKEEECGKNGSDHVS

QKNHGKQEKREPTGPQEPSYLRFIQSLAENTGSVTTDSTVTTSPYAFTQV

TGPYNTFV
```

TETv is derived from mouse Tet2 catalytic domain and contains a deletion. The amino acid sequence ELPKSCEVSGQ (SEQ ID NO:2) is italicized within the sequence of TETv and TETcd sequences shown above and below.

```
TETcd (TET-2 catalytic domain)
                                  (SEQ ID. NO. 3)
QSQNGKCEGCNPDKDEAPYYTHLGAGPDVAAIRTLMEERYGEKGKAIRIE

KVIYTGKEGKSSQGCPIAKWVYRRSSEEEKLLCLVRVRPNHTCETAVMVI

AIMLWDGIPKLLASELYSELTDILGKCGICTNRRCSQNETRNCCCQGENP

ETCGASFSFGCSWSMYYNGCKFARSKKPRKFRLHGAEPKEEERLGSHLQN

LATVIAPIYKKLAPDAYNNQVEFEHQAPDCCLGLKEGRPFSGVTACLDFS

AHSHRDQQNMPNGSTVVVTLNREDNREVGAKPEDEQFHVLPMYIIAPEDE

FGSTEGQEKKIRMGSIEVLQSFRRRRVIRIG*ELPKSC*KKKAEPKKAKTKK

AARKRSSLENCSSRTEKGKSSSHTKLMENASHMKQMTAQPQLSGPVIRQP

PTLQRHLQQGQRPQQPQPPQPQPQTTPQPQPQPQHIMPGNSQSVGSHCSG

STSVYTRQPTPHSPYPSSAHTSDIYGDTNHVNFYPTSSHASGSYLNPSNY

MNPYLGLLNQNNQYAPFPYNGSVPVDNGSPFLGSYSPQAQSRDLHRYPNQ

DHLTNQNLPPIHTLHQQTFGDSPSKYLSYGNQNMQRDAFTTNSTLKPNVH

HLATFSPYPTPKMDSHFMGAASRSPYSHPHTDYKTSEHHLPSHTIYSYTA

AASGSSSSHAFHNKENDNIANGLSRVLPGFNHDRTASAQELLYSLTGSSQ

EKQP*EVSGQ*DAAAVQEIEYWSDSEHNFQDPCIGGVAIAPTHGSILIECAK

CEVHATTKVNDPDRNHPTRISLVLYRHKNLFLPKHCLALWEAKMAEKARK

EEECGKNGSDHVSQKNHGKQEKREPTGPQEPSYLRFIQSLAENTGSVTTD

STVTTSPYAFTQVTGPYNTFV
```

The deleted amino acids correspond to residues 338 to 704 TETcd (shown in italics above). The amino acid sequence ELPKSCEVSGQ (SEQ ID NO:2) contains 5 amino acids from one side of the junction and 5 amino acids from the other side of the junction, as shown above.

In some embodiments, the variant methylcytosine dioxygenase may be a fusion protein. In these embodiments, the variant may have a binding domain that is capable of recognizing and binding to another molecule. Thus, in some embodiments the binding domain is a histidine tag ("His-tag") although a maltose-binding protein, a chitin-binding domain, a SNAP-tag® or a DNA-binding domain, which may include a zinc finger and/or a transcription activator-like (TAL) effector domain are also examples of binding moieties.

Embodiments include a buffered composition containing a purified TETv. For example, the pH of the buffer in the composition is pH 5.5-8.5, for example pH 5.5-7.5, pH 7.5-8.0 or pH 8.0. In various embodiments, the buffered composition may contain glycerol; and/or contains Fe(II), as cofactor, and α-ketoglutarate, as co-substrate, for the enzyme. In some of these embodiments, the composition contains ATP to allow further oxidation of $^{hmC}$ to $^{fC}$ and $^{caC}$; in other embodiments, the composition does not contain dATP that limits the distribution of the oxidized forms of $^{mC}$.

Embodiments include an in vitro mixture that includes a TETv, a βGT, a cytidine deaminase, and/or an endonuclease. The in vitro mixture may further include a polynucleotide substrate and at least dATP. The polynucleotide could be ss or ds, a DNA or RNA, a synthesized oligonucleotide (oligo), chromosomal DNA, or an RNA transcript. The polynucleotide used could be labeled at one or both ends. The polynucleotide may harbor a C, $^{m}$c, $^{hm}$C, $^{fC}$, $^{caC}$ or $^{ghm}$C. In other embodiments, the polynucleotide may harbor a T, U, hydroxymethyluracil ($^{hm}$U), formyluracil ($^{f}$U), or carboxyuracil ($^{ca}$U).

Embodiments provide a TETv, which oxidizes $^{m}$C to $^{hm}$C, $^{f}$C, and/or $^{ca}$C preferably in any sequence context with minimal sequence bias and minimal damage to the DNA substrate compared to BS-seq. TETv may additionally or alternatively oxidize T to $^{hm}$U or $^{f}$U with improved efficiency and reduced bias compared with naturally occurring mouse TET-2 enzyme, or its catalytic domain (TETcd).

In an embodiment of the method, C could be distinguished from $^{m}$C by reacting the polynucleotide of interest with a TETv and a cytidine deaminase wherein only C is converted to U. A further embodiment includes sequencing the polynucleotide treated with the βGT and the cytidine deaminase in which C is converted to U and $^{m}$C is converted to a T and comparing the sequencing results to that of sequencing the untreated polynucleotide to map $^{m}$C and $^{hm}$C location in the polynucleotide.

In another embodiment of the method, both $^{m}$C and $^{hm}$C locations in a polynucleotide are mapped. In this method: (a) the polynucleotide is untreated; (b) reacted with bisulfite reagent; or (c) reacted with GT prior to adding a methylcytosine dioxygenase then treating with bisulfite reagent. (a) through (c) are sequenced and comparison of the sequencing results enables the mapping of $^{m}$C and $^{hm}$C and their differentiation from C: (a) C, $^{m}$C, and $^{hm}$C are all sequenced as C; (b) C is sequenced as C while $^{m}$C and $^{hm}$C as T; and (c) $^{hm}$C is converted to $^{ghm}$C and sequenced as C, C is sequenced as C, and $^{m}$C as T.

In some embodiments, $^{f}$C locations in a polynucleotide are mapped by coupling the oxidation activity of TETv to the activity of a restriction endonuclease or an AP endonuclease specific to $^{hm}$C or $^{fC}/^{caC}$, respectively.

In some aspects, $^{m}$C, $^{hm}$C, or $^{f}$C may be mapped to sites in a polynucleotide using single-molecule sequencing technologies such as Single Molecule Real-Time (SMRT) Sequencing, Oxford Nanopore Single Molecule Sequencing (Oxford, UK) or 10× Genomics (Pleasanton, Calif.). In some embodiments, the method may employ TETv, a cytidine deaminase, and/or GT.

The above-described TETv enzyme can be used as a methylcytosine dioxygenase in any of the methods, compositions or kits summarized above and described in greater detail below.

Kits

Also provided by the present disclosure are kits for practicing the subject method as described above. In certain embodiments, a subject kit may contain: a GT, a methylcytosine dioxygenase and a cytidine deaminase. The components of the kit may be combined in one container, or each component may be in its own container. For example, the components of the kit may be combined in a single reaction tube or in one or more different reaction tubes. Further details of the components of this kit are described above. The kit may also contain other reagents described above and below that may be employed in the method, e.g., a buffer, ADP-glucose, plasmids into which NAs can be cloned, controls, amplification primers, etc., depending on how the method is going to be implemented.

In addition to above-mentioned components, the subject kit may further include instructions for using the components of the kit to practice the subject method. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Utility

In some embodiments, the method can be used to compare two samples. In these embodiments, the method may be used to identify a difference in the pattern of C modification in a test NA fragment relative to the pattern of cytosine modification in a corresponding reference NA. This method may comprise (a) determining the location of all modified C in a test NA fragment using the above-described method to obtain a first pattern of C modification; (b) determining the location of all modified C in a reference NA fragment using the above-described method to obtain a first pattern of C modification; (c) comparing the test and reference patterns of C modification; and (d) identifying a difference in the pattern of cytosine modification, e.g., a change in the amount of $^{m}$C or $^{hm}$C, in the test NA fragment relative to the reference NA fragment.

In some embodiments, the test NA and the reference NA are collected from the same individual at different times. In other embodiments, the test NA and the reference NA collected from tissues or different individuals.

Exemplary NAs that can be used in the method include, for example, NA isolated from cells isolated from a tissue biopsy (e.g., from a tissue having a disease such as colon, breast, prostate, lung, skin cancer, or infected with a pathogen etc.) and NA isolated from normal cells from the same tissue, e.g., from the same patient; NA isolated from cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and NA isolated from normal cells (e.g., cells that are otherwise identical to the experimental cells except that they are not immortalized, infected, or treated, etc.); NA isolated from cells isolated from a mammal with a cancer, a disease, a geriatric mammal, or a mammal exposed to a condition, and NA isolated from cells from a mammal of the same species, e.g., from the same family, that is healthy or young; and NA isolated from differentiated cells and NA isolated from non-differentiated cells from the same mammal (e.g., one cell being the progenitor of the other in a mammal, for example). In one embodiment, NA isolated from cells of different types, e.g., neuronal and non-neuronal cells, or cells of different status (e.g., before and after a stimulus on the cells) may be compared. In another embodiment, the experimental material is NA isolated from cells susceptible to infection by a pathogen such as a virus, e.g., human immunodeficiency virus (HIV), etc., and the reference material is NA isolated from cells resistant to infection by the pathogen. In another embodiment of the invention, the sample pair is represented by NA isolated from undifferentiated cells, e.g., stem cells, and NA isolated from differentiated cells.

In some exemplary embodiments, the method may be used to identify the effect of a test agent, e.g., a drug, or to determine if there are differences in the effect of two or more different test agents. In these embodiments, NA from two or more identical populations of cells may be prepared and, depending on how the experiment is to be performed, one or more of the populations of cells may be incubated with the test agent for a defined period of time. After incubation with the test agent, the genomic DNA from one both of the populations of cells can be analyzed using the methods set forth above, and the results can be compared. In a particular embodiment, the cells may be blood cells, and the cells can be incubated with the test agent ex vivo. These methods can be used to determine the mode of action of a test agent, to identify changes in chromatin structure or transcription factor occupancy in response to the drug, for example.

The method described above may also be used as a diagnostic (which term is intended to include methods that provide a diagnosis as well as methods that provide a prognosis). These methods may comprise, e.g., analyzing C modification from a patient using the method described above to produce a map; and providing a diagnosis or prognosis based on the map.

The method set forth herein may also be used to provide a reliable diagnostic for any condition associated with altered cytosine modification. The method can be applied to the characterization, classification, differentiation, grading, staging, diagnosis, or prognosis of a condition characterized by an epigenetic pattern. For example, the method can be used to determine whether the C modifications in a fragment from an individual suspected of being affected by a disease or condition is the same or different compared to a sample that is considered "normal" with respect to the disease or condition. In particular embodiments, the method can be directed to diagnosing an individual with a condition that is characterized by an epigenetic pattern at a particular locus in a test sample, where the pattern is correlated with the condition. The methods can also be used for predicting the susceptibility of an individual to a condition.

In some embodiments, the method can provide a prognosis, e.g., to determine if a patient is at risk for recurrence. Cancer recurrence is a concern relating to a variety of types of cancer. The prognostic method can be used to identify surgically treated patients likely to experience cancer recurrence so that they can be offered additional therapeutic options, including preoperative or postoperative adjuncts such as chemotherapy, radiation, biological modifiers and other suitable therapies. The methods are especially effective for determining the risk of metastasis in patients who demonstrate no measurable metastasis at the time of examination or surgery.

The method can also be used to determining a proper course of treatment for a patient having a disease or condition, e.g., a patient that has cancer. A course of treatment refers to the therapeutic measures taken for a patient after diagnosis or after treatment. For example, a determination of the likelihood for recurrence, spread, or patient survival, can assist in determining whether a more conservative or more radical approach to therapy should be taken, or whether treatment modalities should be combined. For example, when cancer recurrence is likely, it can be advantageous to precede or follow surgical treatment with chemotherapy, radiation, immunotherapy, biological modifier therapy, gene therapy, vaccines, and the like, or adjust the span of time during which the patient is treated.

In a particular embodiment, a lab will receive a sample (e.g., blood) from a remote location (e.g., a physician's office or hospital), the lab will analyze a NA isolated from the sample as described above to produce data, and the data may be forwarded to the remote location for analysis.

Epigenetic regulation of gene expression may involve cis or trans-acting factors including nucleotide methylation. While cis-acting methylated nucleotides are remotely positioned in a DNA sequence corresponding to an enhancer, these sites may become adjacent to a promoter in a three-dimensional structure for activating or deactivating expression of a gene. Enhancers can be megabases away from the corresponding promoter and thus understanding the relationship between a methylation site in an enhancer and its impact on a corresponding promoter (phasing) over long distances is desirable. Phasing the methylation of a distantly located enhancer to a promoter on which it acts can provide important insights into gene regulation and mis-regulation that occurs in diseases such as cancer.

In order to further illustrate the present invention, the following specific examples are given with the understanding that they are being offered to illustrate the present invention and should not be construed in any way as limiting its scope.

All references cited herein are incorporated by reference.

EXAMPLES

Example 1. Enzyme Based Method for Mapping Methylcytosine and Hydroxymethylcytosine Embodiments of methods described herein provide an unbiased efficient means of mapping $^mC$ and $^{hm}C$ along long stretches of genomic DNA. Such methods describe how to protect biologically relevant DNA modification, such as $^mC$ and $^{hm}C$ in DNA deamination reaction in order to detect and read these modifications. The methods avoid unwanted fragmentation that arises using chemical methods (such as the bisulfite method). The enzymatic methods use one or more of the following enzymes: a cytidine deaminase, a methylcytosine dioxygenase and a GT.

Examples are provided that utilize a cytidine deaminase described in U.S. Pat. No. 9,121,061 (specifically APOBEC3A in this example) although other cytidine deaminases may be used (as discussed above). The Examples provided herein utilize Deaminase-seq. Deaminase-seq refers to the pathway that depends on a deaminase reaction leading to sequencing to detect modified cytosine. The pathway shown in FIG. 1A may further include a GT such as 3) which may be combined with the methylcytosine dioxygenase in one reaction mix or added sequentially in one reaction vessel. A novel methylcytosine dioxygenase is described herein that provides more efficient and unbiased conversion of $^mC$ and $^{hm}C$ to $^{Ca}C$ then does wild type human or mouse TET proteins. Typically, Deaminase-Seq includes the following steps: treating genomic DNA or DNA library preparations (such as Ultra II Library prep with protected adaptors (NEB)), the use of one or more of TET2 deoxygenase and GT enzymes for example, TET2 deoxygenase followed by GT (BGT) or in parallel with GT, removal of enzyme activity by for example heat denaturation followed by deamination using for example Apobec A3A, amplification and then sequencing in an Illumina sequencer, PacBio sequencer or other commercially available sequencing device. Further experimental details for embodiments are provided below.

A. Discrimination of Methylcytosine from Unmodified Cytosine in Genomic DNA Using an Engineered Methylcytosine Dioxygenase (TETv) and a Cytidine Deaminase (APOBEC)

(i) Mouse NIH/3T3 DNA (250 ng) was reacted with TETv (8 µM) in 50 ul Tris buffer at 37° C. for 1 hour and the oxidized DNA was column purified (Zymo Research, Irvine, Calif.).

(ii) The DNA was then heated to 70° C. in presence of 66% of formamide in a thermocycler and then placed on ice. RNase A (0.2 mg/ml), BSA (10 mg/ml) and cytidine deaminase (0.3 mg/ml) were added (see also Bransteitter et al. PNAS (2003) vol 100, 4102-4107) and incubated for 3 hours at 37° C. DNA was column purified (Zymo Research, Irvine, Calif.). Following PCR with U-bypass DNA polymerase (New England Biolabs, Ipswich, Mass.) using Primer 1 AATGAAGGAAATGAATTTGGTAGAG (SEQ ID NO:6) and Primer 2 TCCCAAATACATAAATCCACACTTA (SEQ ID NO:7), the products were cloned using the NEB PCR Cloning Kit (New England Biolabs, Ipswich, Mass.) and the clones were subjected to Sanger sequencing. Sequencing results are summarized in FIG. 2A. Empty dots represent unmodified CpG sites in the PCR fragment, black dots represent $^m$CpG sites in the PCR fragment.

B. Discrimination of Hydroxymethylcytosine from Unmodified Cytosine and Methylcytosine Using T4-βGT (New England Biolabs, Ipswich, Mass.) and Cytidine Deaminase (i) DNA was reacted with T4-βGT (20 Units) in the presence of UDP (1 µl) in a volume of 50 µl at 37° C. for 1 hour and then column purified DNA. The method followed the steps in (ii) above. Sequencing results are summarized in FIG. 2B. Empty dots represent unmodified CpG sites in the PCR fragment, black dots represent $^{hm}$CpG sites in the PCR fragment.

Example 2. Ss DNA is not Damaged During Methylcytosine Deoxygenase. DNA Glucosyltransferase or Cytidine Deaminase Treatment The demonstration that DNA damage does not occur during the analysis of modified bases in ss DNA is a significant advantage of the current bisulfite method commonly used for methylome analysis (see FIG. 3A-3E). It is the lack of damage as shown in FIG. 3A-3B, 3D-3E that makes it possible to obtain phase data.

Mouse E14 genomic DNA was sheared to fragments (Covaris, Woburn, Mass.) of a size of approximately 15 kb and selected and purified using AMPure® XP beads (Beckman Coulter, Brea, Calif.). The DNA were then treated as follows:

(a) Control DNA. The 15 kb fragments of DNA was denaturated to ssDNA at 70° C. in presence of 66% of formamide for 10 minutes.

(b) Bisulfite converted DNA. The 15 kb fragments of DNA were treated with sodium bisulfite using EZ DNA Methylation-Gold™ Kit (Zymo Research, Irvine, Calif.), according to the instruction manual.

(c) T4-βGT and cytidine deaminase (APOBEC3A) treated DNA. 15 kb DNA fragments were glucosylated and then deaminated as described in Example 1.

(d) TETv and cytidine deaminase (APOBEC3A) treated DNA. 15 kb DNA fragments were treated with TETv, and then deaminated as described above.

Initially the DNA from samples (a)-(d) were examined on an Agilent RNA 6000 pico chip (Agilent, Santa Clara, Calif.). The data is given in FIG. 3E (y-axis is the fluorescent units while the X-axis is size (daltons). The light blue line represents the denatured ss DNA of the 15 kb AMPure size selected fragments, which is also the control. The red line is APOBEC deamination on glucosylated DNA. The dark blue is DNA deamination on TETv oxidized DNA. And the green is bisulfite treated DNA. When comparing to the control, both cytidine deaminase treated substrates show no significant difference in size distribution whereas the bisulfite treated DNA reduced in size greatly, showing significant DNA degradation.

The 15 Kb treated DNA from samples (a)-(d) was also PCR amplified to produce amplicons of 4229 bp, 3325 bp, 2018 bp, 1456 bp, 731 bp and 388 bp using Phusion® U (ThermoFisher Scientific, Waltham, Mass.) DNA polymerase.

Products were analyzed on 1% agarose gels and the results provided in FIG. 3B-3E. The results show that the treatment of DNA with cytidine deaminase, GT and the methylcytosine dioxgenase did not cause detectable fragmentation. In contrast, bisulfite treatment caused the DNA to fragment to fragments no larger than 731 bp.

388
(SEQ ID NO: 8)
TAGGATAAAAATATAAATGTATTGTGGGATGAGG (SEQ ID NO: 9)
AAAACATATAACCCCCTCCACTAATAC 731
(SEQ ID NO: 10)
AGATATATTGGAGAAGTTTTGGATGATTTGG (SEQ ID NO: 11)
AAAACATATAACCCCCTCCACTAATAC 1456
(SEQ ID NO: 12)
TAAGATTAAGGTAGGTTGGATTTGG (SEQ ID NO: 13)
TCATTACTCCCTCTCCAAAAATTAC 2018
(SEQ ID NO: 14)
AAGATTTAAGGGAAGGTTGAATAGG (SEQ ID NO: 15)
ACCTACAAAACCTTACAAACATAAC 3325
(SEQ ID NO: 16)
TGGAGTTTGTTGGGGGTTTGTTGTTTAAG (SEQ ID NO: 17)
TCTAACCCTCACCACCTTCCTAATACCCAA 4229
(SEQ ID NO: 18)
TGGTAAAGGTTAAGAAGGGAAGATTGTGGA (SEQ ID NO: 19)
AACCCTACTTCCCCCTAACAAATTTTCAAC

Example 3. Synthesis of an Adaptor for NGS Library Construction where all Cytosines are Protected from Deamination in the Presence of Cytidine DNA Deaminases This example describes the experiment, confirming that pyrrolo-dC is not a substrate for cytidine deaminase, and may be used to synthesize a protected adaptor suitable for a sequencing platform such as Illumina.

Figure 4A:
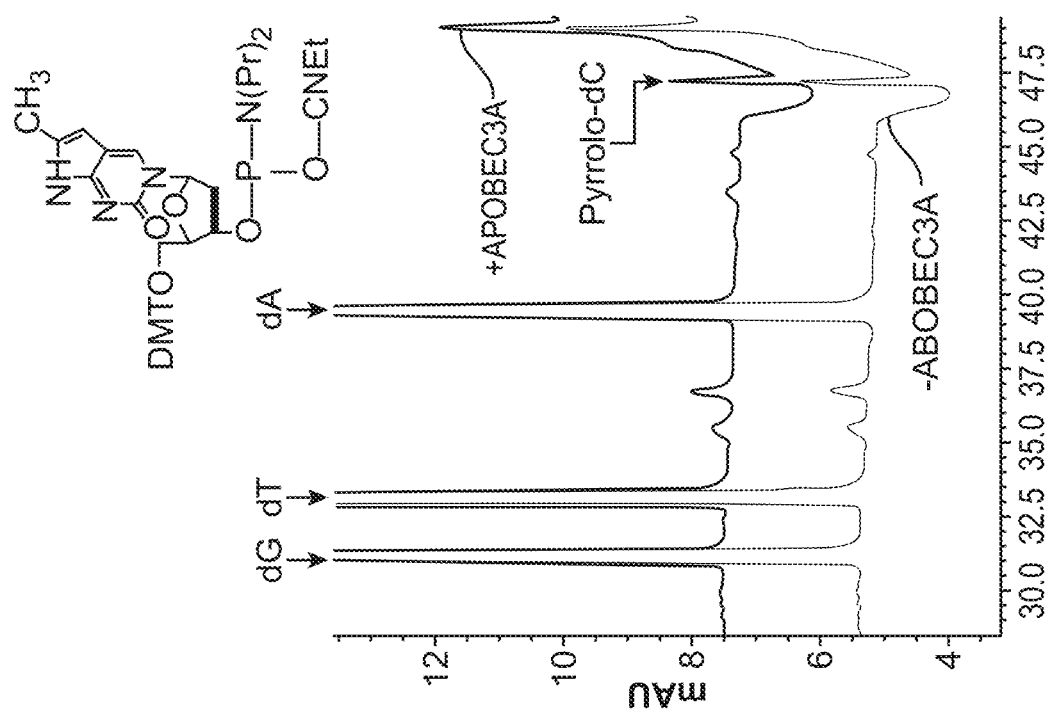
FIGS. 4A and 4B shows that cytidine deaminase does not deaminate the modified base-Pyrrolo-dC (Glen Research, Sterling, Va.). This modified base can be used in Illumina NGS library construction to protect C in the adapters ligated to the ends of DNA fragments in the library from deamination prior to cytidine deaminase treatment.
Figure 4B:
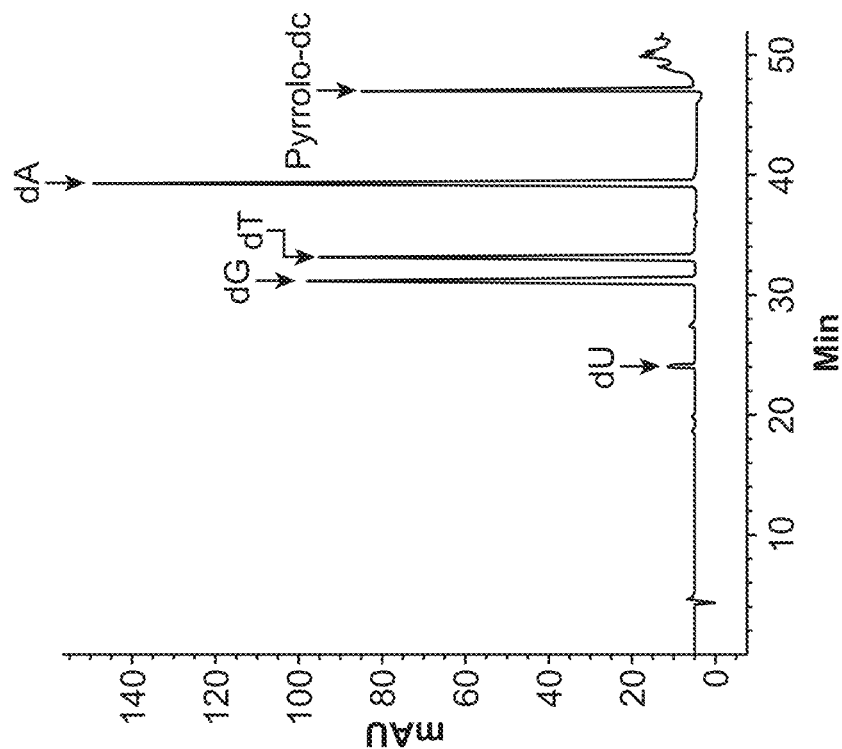

A reaction mixture was made containing 2 µM 44 bp ssDNA oligonucleotide containing a single Pyrrolo-dC (5'-ATAAGAATAGAATGAATXGTGAAATGAATAT-GAAATGAATAGTA-3', X=Pyrrolo-dC) (SEQ ID NO:4), 50 mM BIS-TRIS pH6.0, 0.1% TritonX-100, 10 lag BSA, 0.2 lag RNase A, and 0.2 µM purified recombinant cytidine deaminase. This was incubated at 37° C. for 16 hours. The DNA was recovered by using DNA Clean and Concentrator™ Kit (Zymo Research, Irvine, Calif.). A mixture of nuclease P1w, Antarctic phosphatase (and DNase I was used to digest purified ss DNA substrate to nucleosides. LC-MS was performed on an Agilent 1200 series (G1315D Diode Array Detector, 6120 Mass Detector) (Agilent, Santa Clara, Calif.) with Waters Atlantis T3 (4.6×150 mm, 3 mm, Waters, Milford, Mass.) column with in-line filter and guard column. The results are shown in FIGS. 4A and 4B. Expected peaks were observed in each sample, and no changes were detected after the treatment with cytidine deaminase (MS: m/z=265). Modified adaptor for NGS library construction was synthesized as 65-mer ss DNA using standard phosphoramidite chemistry (Glen Research Sterling, Va.) on an AB1394 Synthesizer (Applied Biosystems, Foster City, Calif.). Pyrrolo phosphoramidite and purification columns were purchased from Glen Research, Sterling, Va. Oligonucleotide was deprotected according to the manufacturer's recommendations, purified using Glen-Pak DMT-ON columns, desalted using Gel-Pak size-exclusion columns.

An example of a Pyrrolo dC adaptor sequence is provided below, where X=Pyrrolo-dC:

```
                                        (SEQ ID NO: 5)
5'/5Phos/GATXGGAAGAGXAXAXGTXTGAAXTXXAGTX/deoxyU/
AXAXTXTTTXXXTAXAXGAXGXTXTTXXGATCT (also see FIGS.
4A and 4B).
```

Example 4. Whole Genome Methylome Analysis

To explore whether any sequence bias occurred and also efficiency of the methodology, mouse ES cell genomic DNA was sheared to 300 bp fragments with Covaris S2 sonicator (Covaris) for library preparation with the NEBNext® Ultra™ DNA Library Prep Kit for Illumina® according to the manufacturer's instructions for DNA end repair, methylated adapter ligation, and size selection. The sample was then denatured by heat. A Pyrrolo-dC NEBNext adaptor (New England Biolabs, Ipswich, Mass.) was ligated to the dA-tailed DNA followed by treatment with NEB USER™ (New England Biolabs, Ipswich, Mass.).

| Adaptor Ligation Reaction Component | µl |
|---|---|
| dA-tailed DNA | 65 |
| Pyrrolo dC NEBNext adaptor (5 µM) | 2 |
| Blunt/TA Ligase Master Mix | 15 |
| Ligation Enhancer | 1 |
| Total volume | 83 |

Three libraries were created. A first library was sodium bisulfite treated with EZ DNA Methylation-Gold Kit. A second library was treated with EpiTect® Bisulfite Kit Cat. No. 59104 (Qiagen, Valencia, Calif.) according to instruction manual. A third library was treated according to Example 1. The libraries were PCR amplified using NEBNext Q5® Uracil PCR Master Mix; NEBNext Universal PCR Primer for Illumina (15 µM) and NEBNext Index PCR Primer for Illumina (15 µM) (all commercially available at New England Biolabs, Ipswich, Mass.).

TABLE 1

Suggested PCR cycle numbers for mouse ES cell genomic DNA.

| DNA input | Number of PCR cycles |
|---|---|
| 1 µg | 4~7 |
| 100 ng | 8~10 |
| 50 ng | 9~11 |

The results are shown in FIGS. 5-9.

Figure 5:
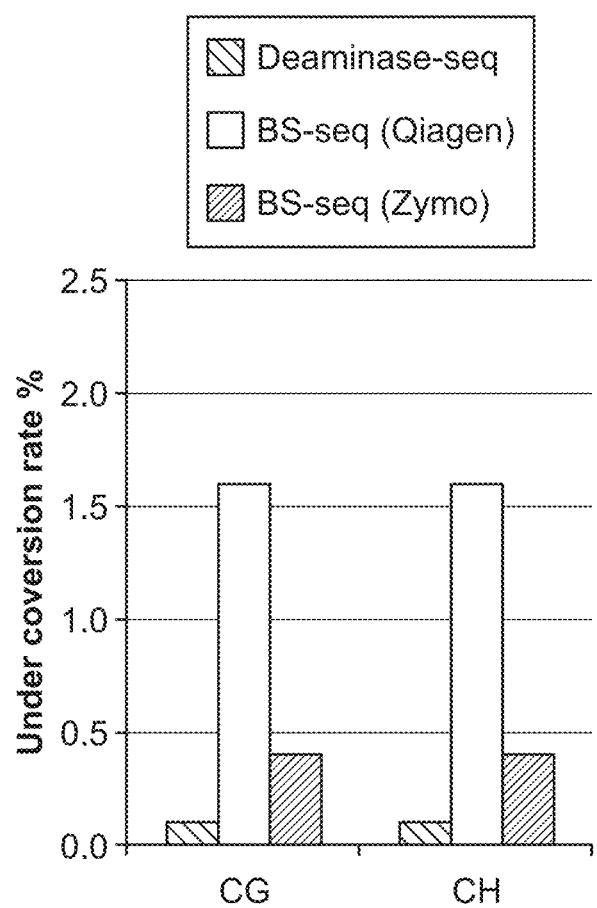
FIG. 5 shows that the method described in Example 4 that provides sequences from Next generation sequencing (NGS) using an Illumina platform as an example of Deaminase-seq provides superior conversion efficiency compared with BS-seq. Unmethylated lambda DNA was used as a negative control to estimate the non-conversion error rate (methylated C calls/total C calls). CD$^mC$ reaction (left slashes) has the smallest error rate of 0.1% for both CpG and CH (H=A,C,T) context. Bisulfite conversion using Zymo kit (right slashes) has 3 times higher error rate than the method shown in FIGS. 1A and 1B (0.4%), and bisulfite conversion by Qiagen (white) has even higher error rate of 1.6% for CpG context and 1.5% for CH context.
Figure 6A:
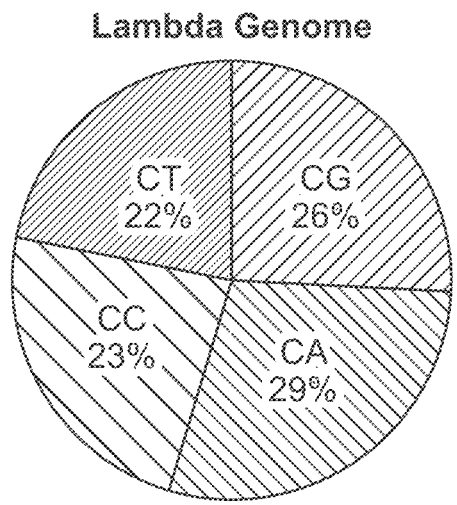
FIG. 6A-6D shows that Deaminase-seq displays no systematic sequence preference while BS-seq generates a significant amount of conversion errors most notably in a CA context. Pie charts depict the numbers and percentages of false positive methylation calls in each C dinucleotide context in the unmethylated lambda genome by different methods.
Figure 6B:
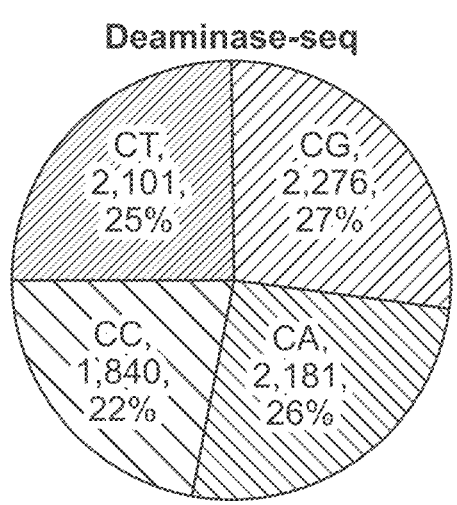
Figure 6C:
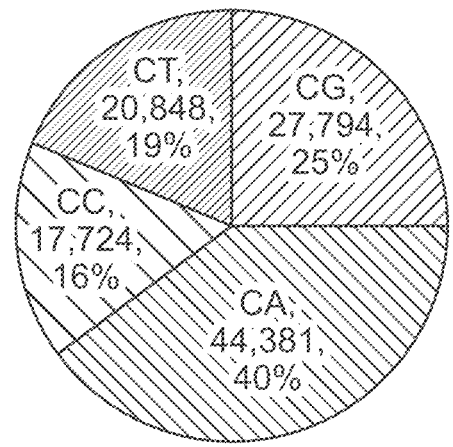
Figure 6D:
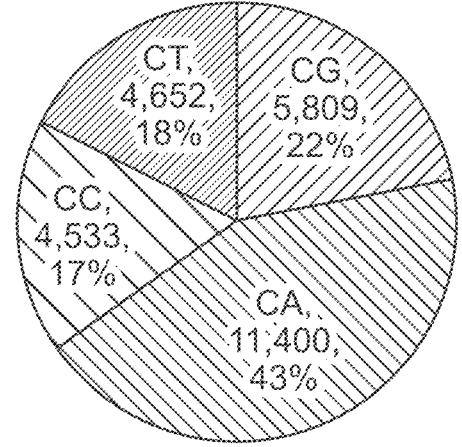
Figure 7:
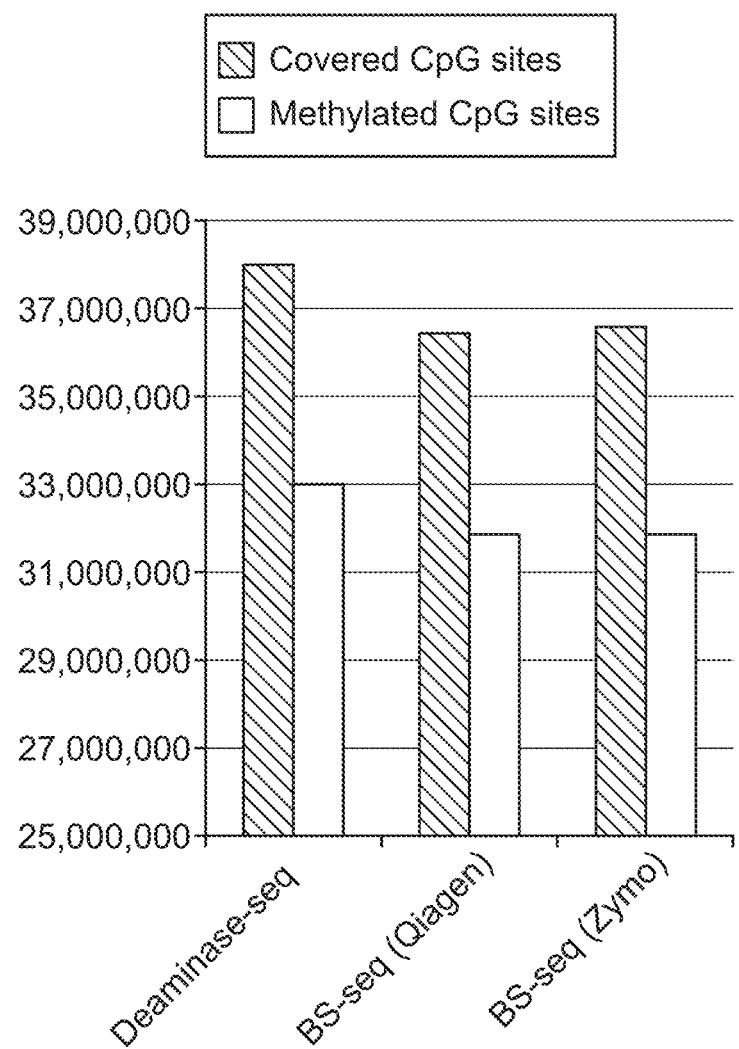
FIG. 7 shows that Deaminase-seq (Illumina) covered more CpG sites and detected more methylated CpG sites than both BS-seq libraries using the same library analysis and the same number of sequencing reads demonstrating that Deaminase-seq is a more efficient and cost effective method than BS-seq.
Figures 8A, 8B, 8C:
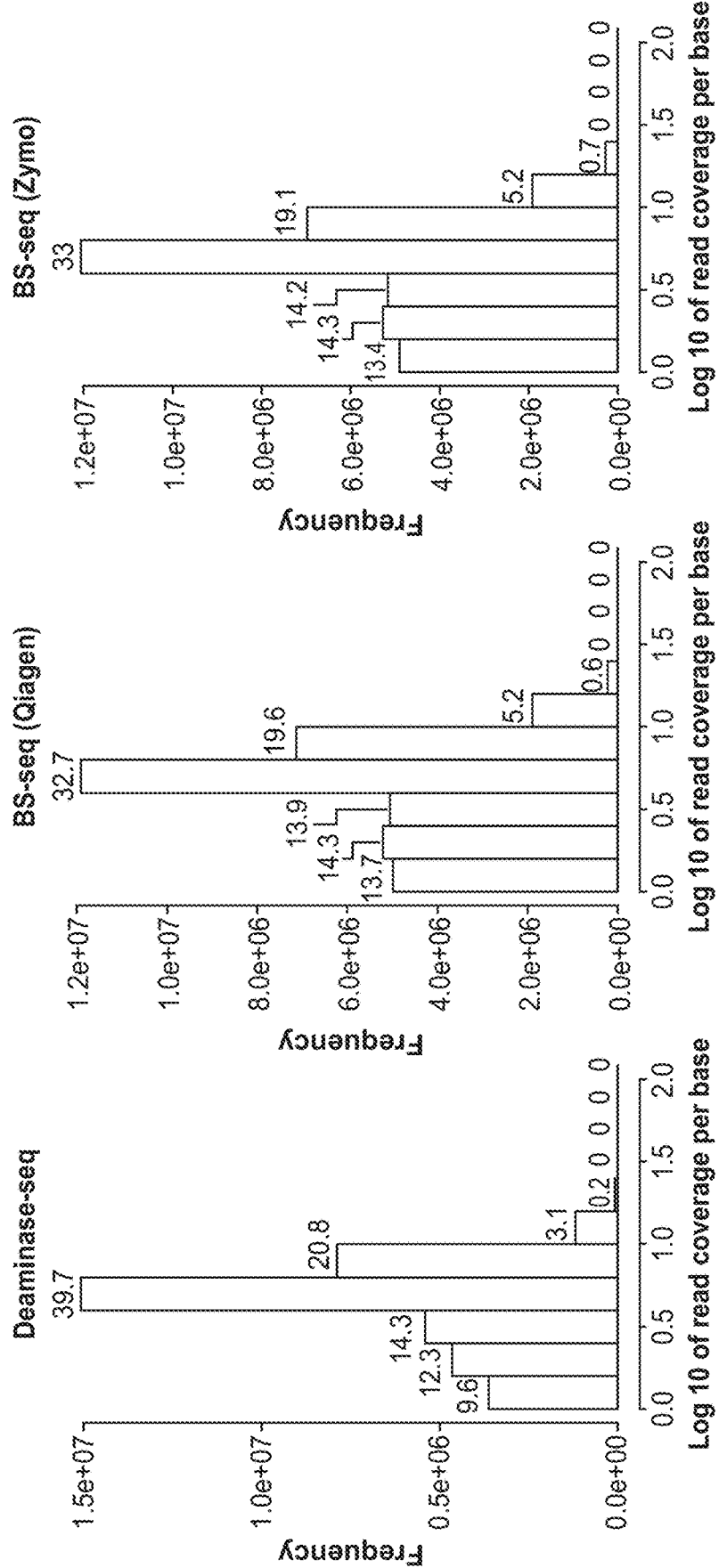
FIG. 8A-8C shows that Deaminase-seq provides an even genome-wide sequence coverage in the mouse genome from Illumina generated reads of overlapping fragments. Three histograms of CpG coverage are shown where the 3 methods have the same mean (5×) and median (4×) sequencing depth for CpG sites. However, Deaminase-seq has fewer outliers (sites with very low or very high copy numbers) when compared with BS-seq kits from Zymo and Qiagen. Three data sets are shown in which, library size normalized.
Figure 9:
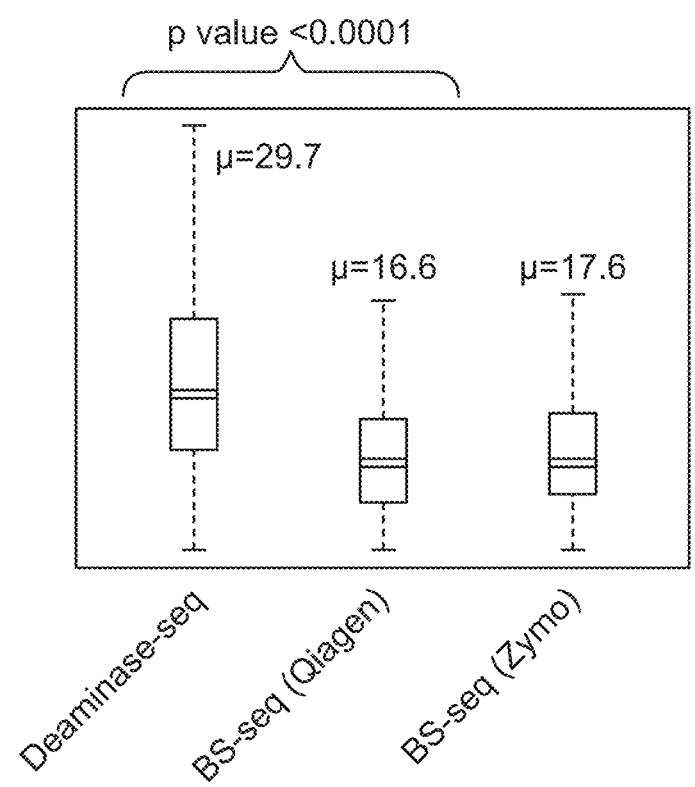
FIG. 9 shows that Deaminase-seq provides higher coverage in CpG islands than BS-seq for the same number of sequencing reads, Deaminase-seq gives nearly 2 times as much coverage as BS-seq in the CpG islands.

Deaminase-seq did not display strong sequence preference whereas both BS-seq methods produced more non-conversion errors (FIG. 5). Moreover, Deaminase-seq provided results that accurately reflected the number of C in a DNA regardless of the nature of the adjacent nucleotide in contrast to BS-seq which showed significant biases for CA. (FIG. 6A-6D) With the same normalized library size of 336 million reads, Deaminase-seq library covered 1.5 million more CpG dinucleotide sites than both BS-seq libraries and in total has coverage for 38.0 million single CpG dinucleotide i.e., 89% of the entire mouse genome (FIG. 7). Deaminase-seq provides a more even sequencing coverage across the entire genome with few outliers with very low or very high copy numbers (FIG. 8A-8C). As a result, Deaminase-seq gives nearly 2 times as many reads as BS-seq in the CpG islands (FIG. 9), which are among the most important genomic regions in epigenetic studies.

Figure 10:
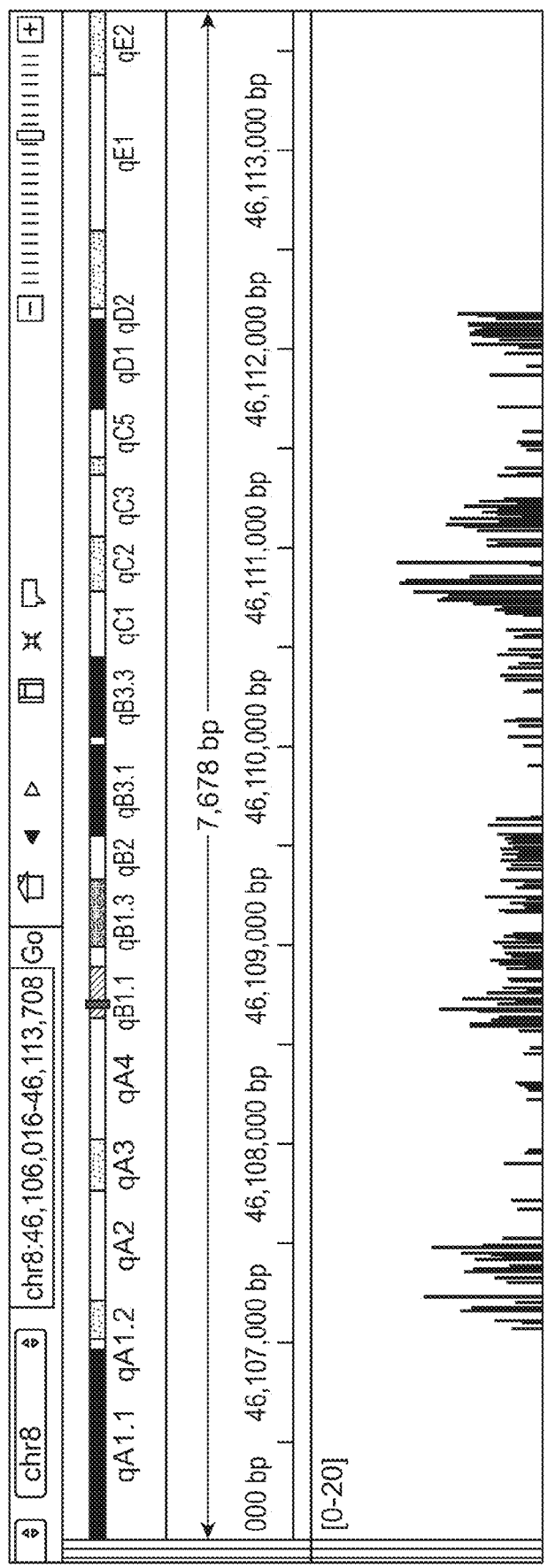
FIG. 10 provides a loci specific map of $^{hm}C$ on a genomic fragment from mouse chromosome 8. Deaminase-seq (FIGS. 1A and 1B) accurately detects $^{hm}C$ of large fragments (5 Kb) at base resolution enabling phasing of DNA modifications and phase DNA modifications together with other genomic features such as SNPs or variants.

A 5.4 kb fragment from glucosylated and deaminated mouse embryonic stem cell genomic DNA (chromosome 8) was sheared to 300 bp and a library of the fragmented DNA was made using the protocol described above and sequenced on Illumina sequencer. This method accurately identified hmC at single base resolution across the entire 5.4 kb region (FIG. 10).

Example 5. $^mC$ and $^{hm}C$ Phasing with SMRT Sequencing (Pacific Biosystems)

Figure 11A:
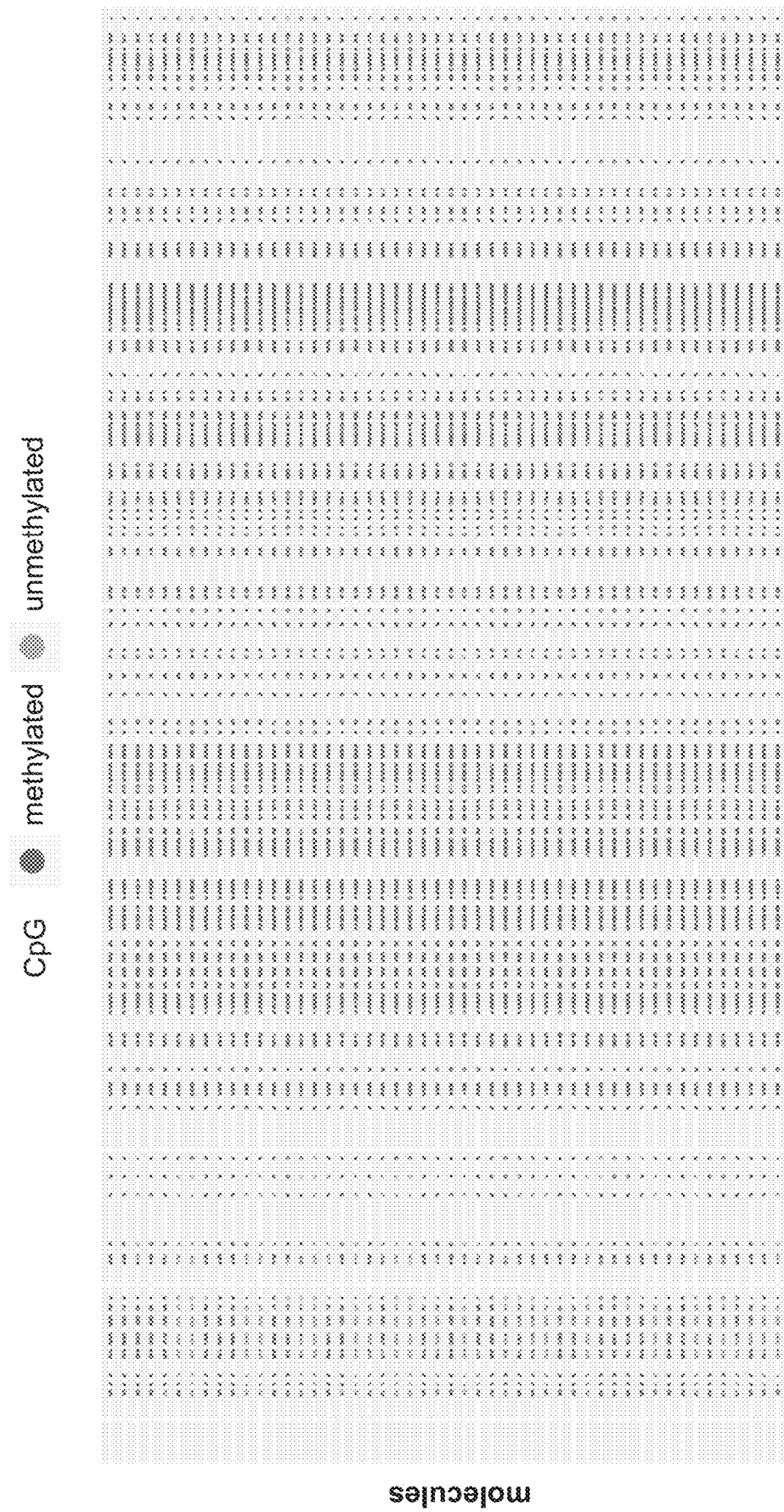
FIG. 11A-11B shows a $^mC$ and $^{hm}C$ profile at single-molecule level across the 5.4 kb region generated by PacBio sequencing. Each row represents one DNA molecule. Each CpG site in the 5.4 kb region was represented by a dot. C modification states were denoted by color.
Figure 11B:
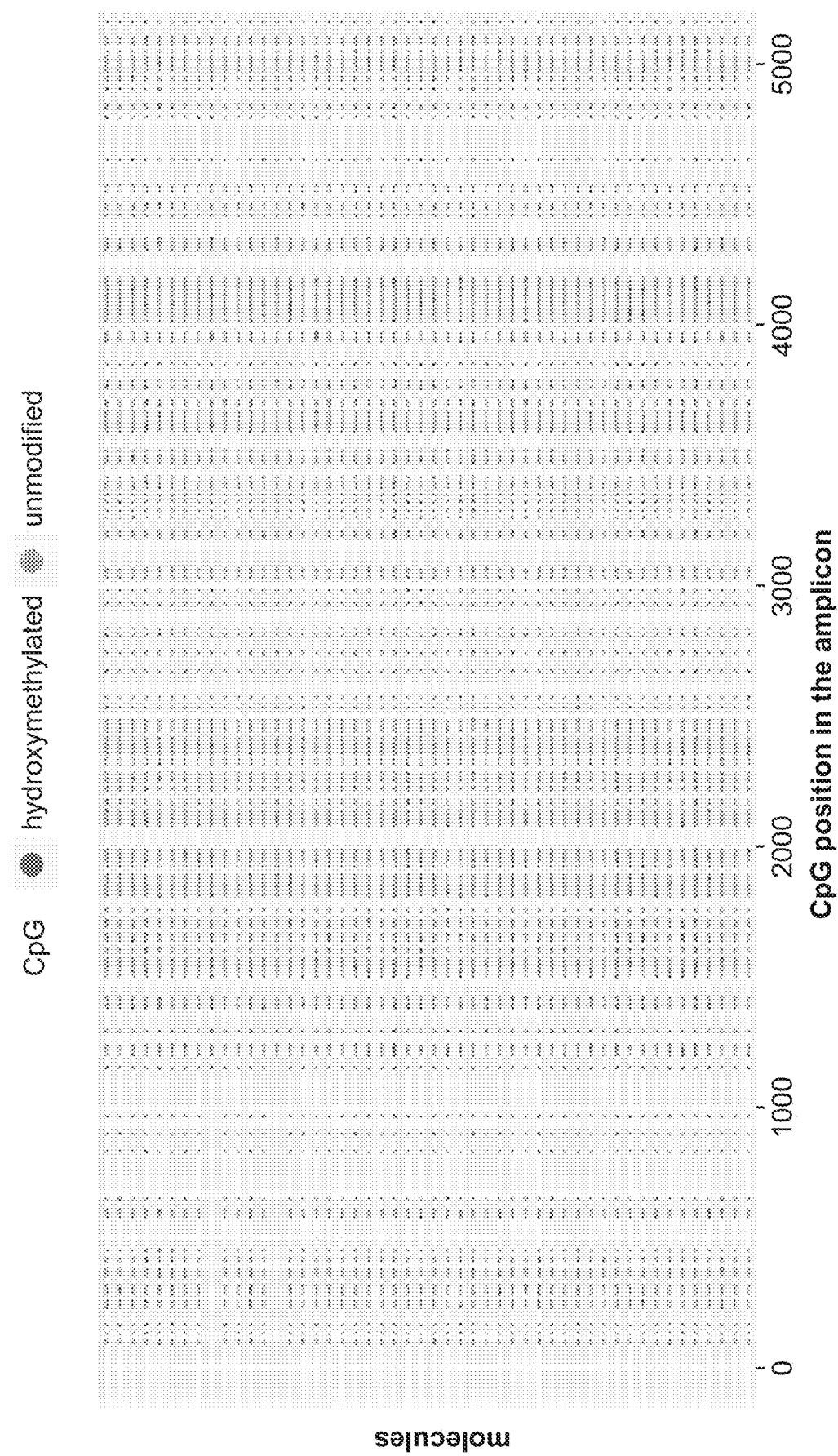

Embodiments of the methods described have generated phased genomic maps of epigenetic modifications over regions that are limited only by the DNA polymerase used to amplify the DNA of interest. Should amplification not be utilized, whole genomes could be analyzed using these methods. A typical example is provided herein with results shown in FIGS. 11A and 11B for a genomic region of 5.4 Kb.

Mouse brain genomic DNA was treated as described in FIGS. 1A and 1B namely by reacting aliquots of the DNA with (a) TETv+βGT treatment (for $^mC/^{hm}C$ detection) and (b) βGT treatment (for $^{hm}C$ detection) respectively. The products of these enzyme reactions were deaminated (cytidine deaminase e.g. APOBEC3A). A 5.4 kb fragment on chromosome 8 was then amplified from the deaminated DNA by PCR. After purification, the 5.4 kb amplicons were used to construct PacBio SMRT libraries following the "Amplicon template preparation and sequencing" protocol (Pacific Biosystems, Menlo Park, Calif.). One library was prepared for each modification type and was loaded onto SMRT cell using the MagBead method. The two libraries were sequenced on a PacBio RSII machine. Consensus sequences of individual sequenced molecules (Read of Insert) were generated by the "RS_ReadsOf Insert" protocol using the SMRT portal and were mapped to the mouse reference genome using the Bismark algorithm. The modification states of all the CpG sites across the 5.4 kb were determined for individual molecule independently. The results show that this 5.4 kb region was heavily methylated across the entire region except for its 5' end. The molecules can be divided into 2 distinct populations: either hyper-methylated at 5' end or methylation depleted at 5' end. In comparison, $^{hm}C$ exists in a few loci and is more dynamic between molecules.

Example 6. Methylation Phasing of Long DNA Fragments (More than 10 kb Long) Using DD-Seq and Partitioning Technologies Such as 10× Genomics ss long converted DNA fragments as describe in Example 5 are purified and 1 ng of the DNA is subject to 10× genomics GemCode™ Platform (10× Genomics, Pleasanton, Calif.). DNA is partitioned into droplets together with droplet-based reagents. The reagent contains gel beads with millions of copies of an oligonucleotides and a polymerase that reads through uracil such as Phusion U. Each oligonucleotide includes the universal Illumina-P5 Adaptor (Illumina, San Diego, Calif.), a barcode, Read 1 primer site and a semi-random N-mer priming sequence. The partitioning is done in such a way that statistically, one or several ss converted long DNA fragments are encapsulated with one bead. The beads dissolved after partitioning, release the oligonucleotides. The semi-random N-mer priming sequence anneals randomly on the ss DNA fragment and polymerase copied the template ss DNA. Droplets are dissolved, DNA is sheared through physical shearing and after end repair and dA tailing, and the right adaptor is ligated to the ss DNA. Amplification of the library is done using the standard Illumina primers and sequenced using standard Illumina protocol as well.

Example 7. Activity Comparison of mTET2CD with TETv on Genomic DNA

TET2cd (3 µM)(SEQ ID NO: 3) or TETv (SEQ ID NO:1) was added to 250 ng IMR90 gDNA (human fetal lung fibroblasts) substrate in a Tris buffer pH 8.0 and the reaction was initiated with the addition of 50 µM FeSO4. The reaction was performed for 1 hour at 37° C. Subsequently, the genomic DNA was degraded to individual nucleotides and analyzed by mass spectrometry.

Figure 12A:
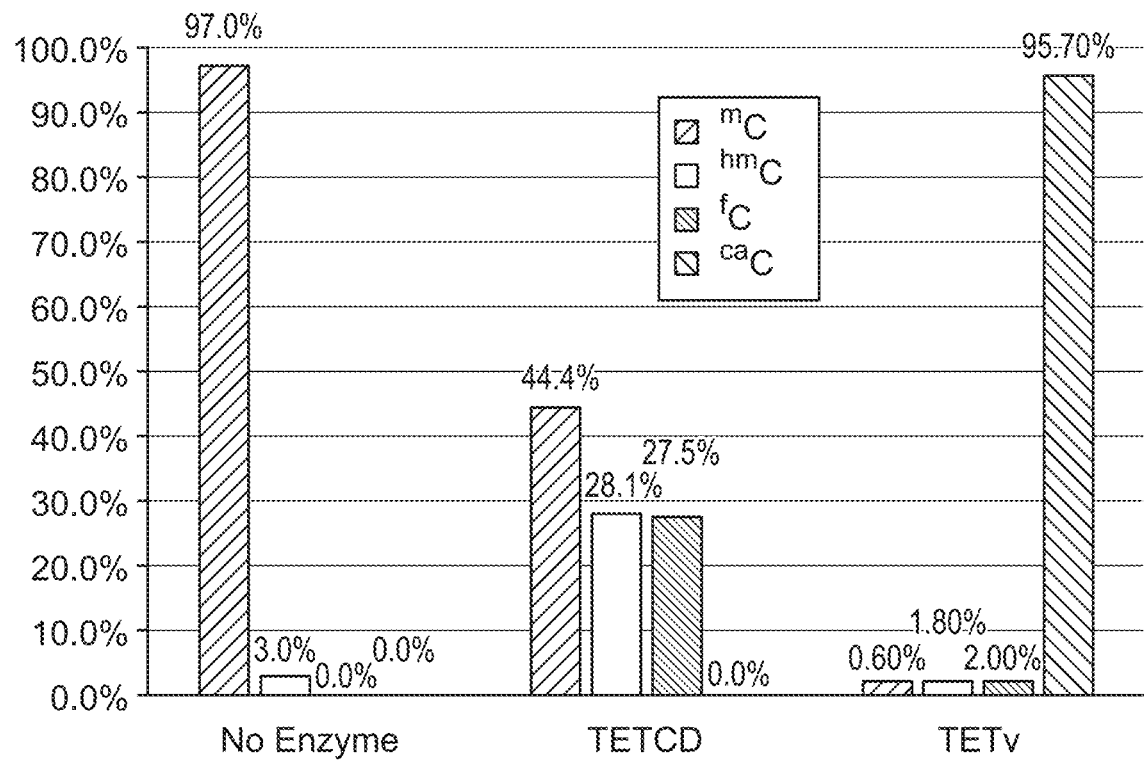
FIG. 12A shows an activity comparison of mouse TET2 catalytic domain (TETcd; SEQ ID NO:3) with TETv (SEQ ID NO:1) on sheared 3T3 genomic DNA.
Figure 12B:
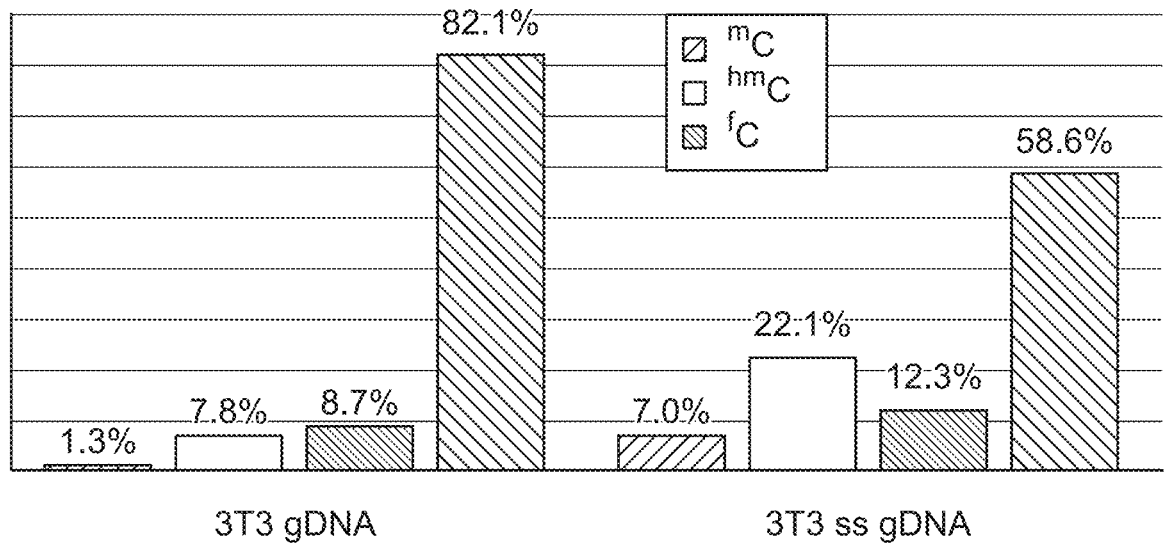

The results provided in FIGS. 12A and 12B show that in the absence of enzyme, $^{m}C$ is the predominant modified nucleotide in the DNA with a small amount of $^{hm}C$. In the presence of mTET2CD, some but not all $^{m}C$ was converted to $^{hm}C$ and a subset of these nucleotides were converted to $^{f}C$ suggesting incomplete activity and/or bias. In contrast, TETv converted substantially all the $^{m}C$ to $^{ca}C$ with very little intermediate substrate. The results are shown in FIG. 12A.

Example 8: Activity of TETv on Ss and Ds Mouse Genomic DNA

Mouse 3T3 gDNA was sheared to 1500 bp and purified using Qiagen nucleotide purification kit (Qiagen, Valencia, Calif.). Fragmented gDNA was denatured to form ss fragments by heating at 95° C. for 5 minutes followed by immediate cool down on ice for 10 minutes. 250 ng sheared 3T3 gDNA substrate was with TETv as described in Example 8 under similar reaction conditions. Analysis of modified bases was done according to Example 8. The results are shown in FIG. 12B.

Figure 13:
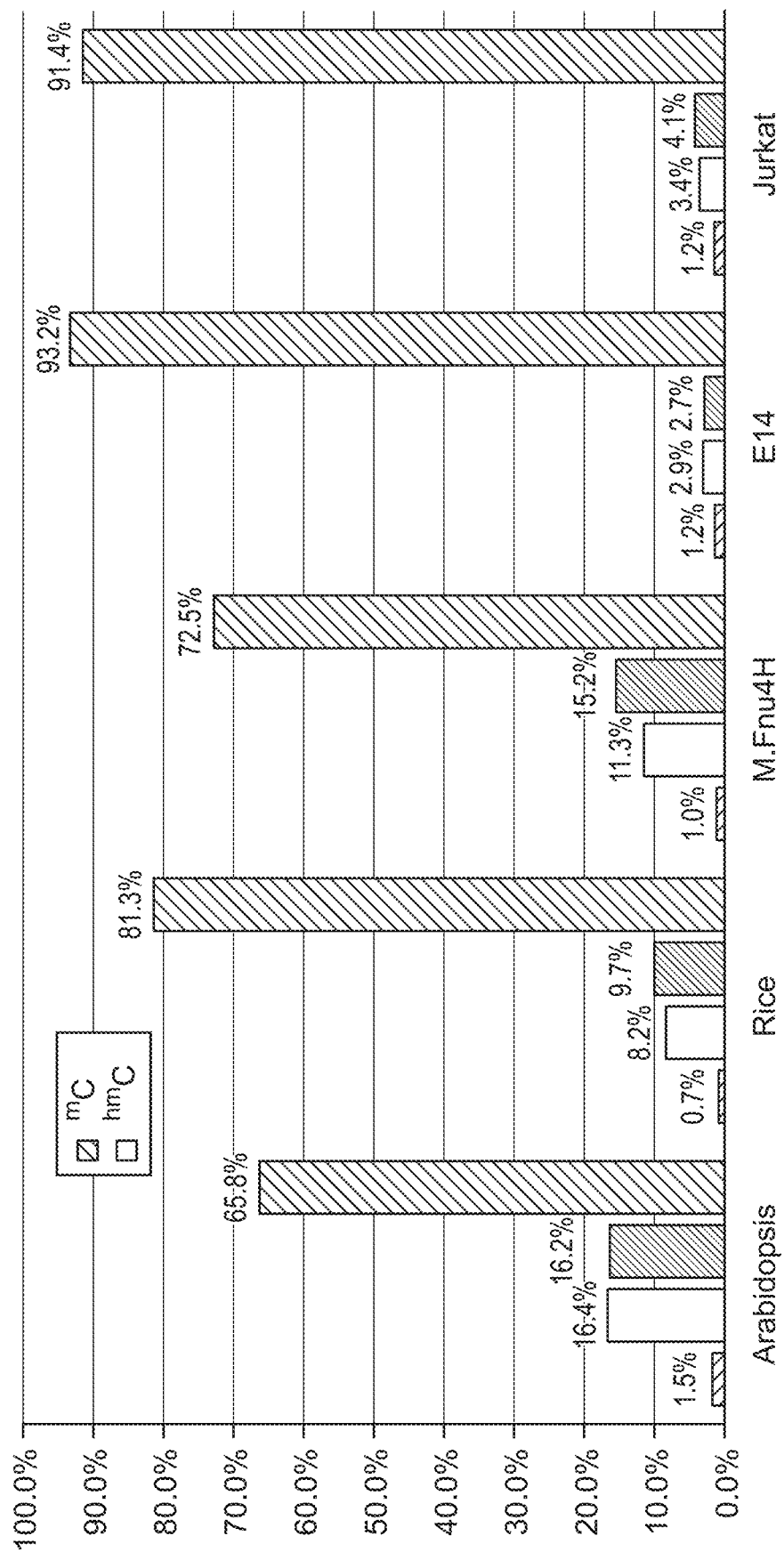
FIG. 13 shows that TETv exhibits very low sequence bias and is context independent for $^mC$ as demonstrated for 5 cell lines (*Arabidopsis*, rice, M.Fnu4H, E14 and Jurkat).

Example 9: TETv Exhibits Very Low Sequence Bias where Analysis of 5 Genomes Show that the Property is not Substrate Specific The reaction was performed according to Example 7 using genomic DNA from 5 different cell types. Low sequence specificity is preferable as it denotes lack of sequence bias by the enzyme. The results are shown in FIG. 13.

Example 10: DNA Treated with TETv is Intact

MspI is sensitive to oxidized forms of $^{m}C$ but not $^{m}C$. The reaction was performed according to Examples 8. TETv was used at 3 µM and HpaII plasmid substrate at 100 ng. 20 U of BamHI (to linearize the plasmid) and 50 U of MspI in CutSmart® buffer (pH 7.9) (New England Biolabs, Ipswich, Mass.) were added for 1 hour at 37° C. in 20 µL total volume.

Figure 14:
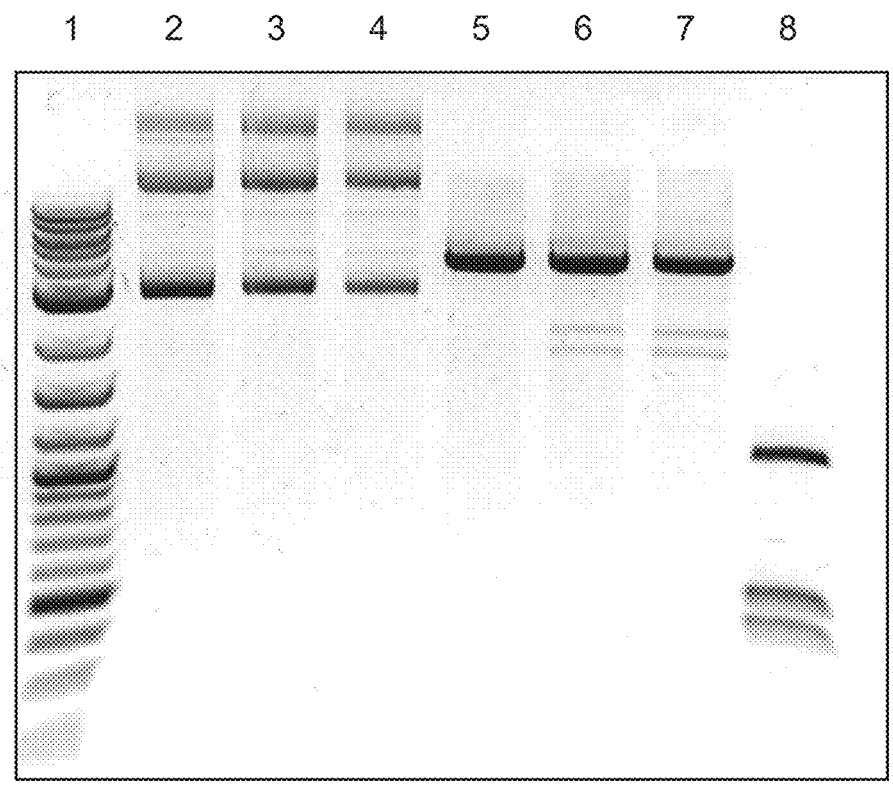
FIG. 14 shows that TETv does not degrade DNA as determined from the preservation of supercoiled DNA after enzyme treatment. Lane 1 is a size ladder. Lane 2 is substrate plasmid only, Lane 3 is supercoiled plasmid+323 pmol of TETv; Lane 4 is supercoiled plasmid+162 pmol TETv; Lane 5 is supercoiled plasmid+162 pmol TETv; Lane 6 is Substrate plasmid+323 pmol TETv+BamHI+MspI; Lane 7 is Substrate plasmid+162 pmol TETv+BamHI+MspI; and Lane 8 is Substrate plasmid+BamHI+MspI.
Figure 15:
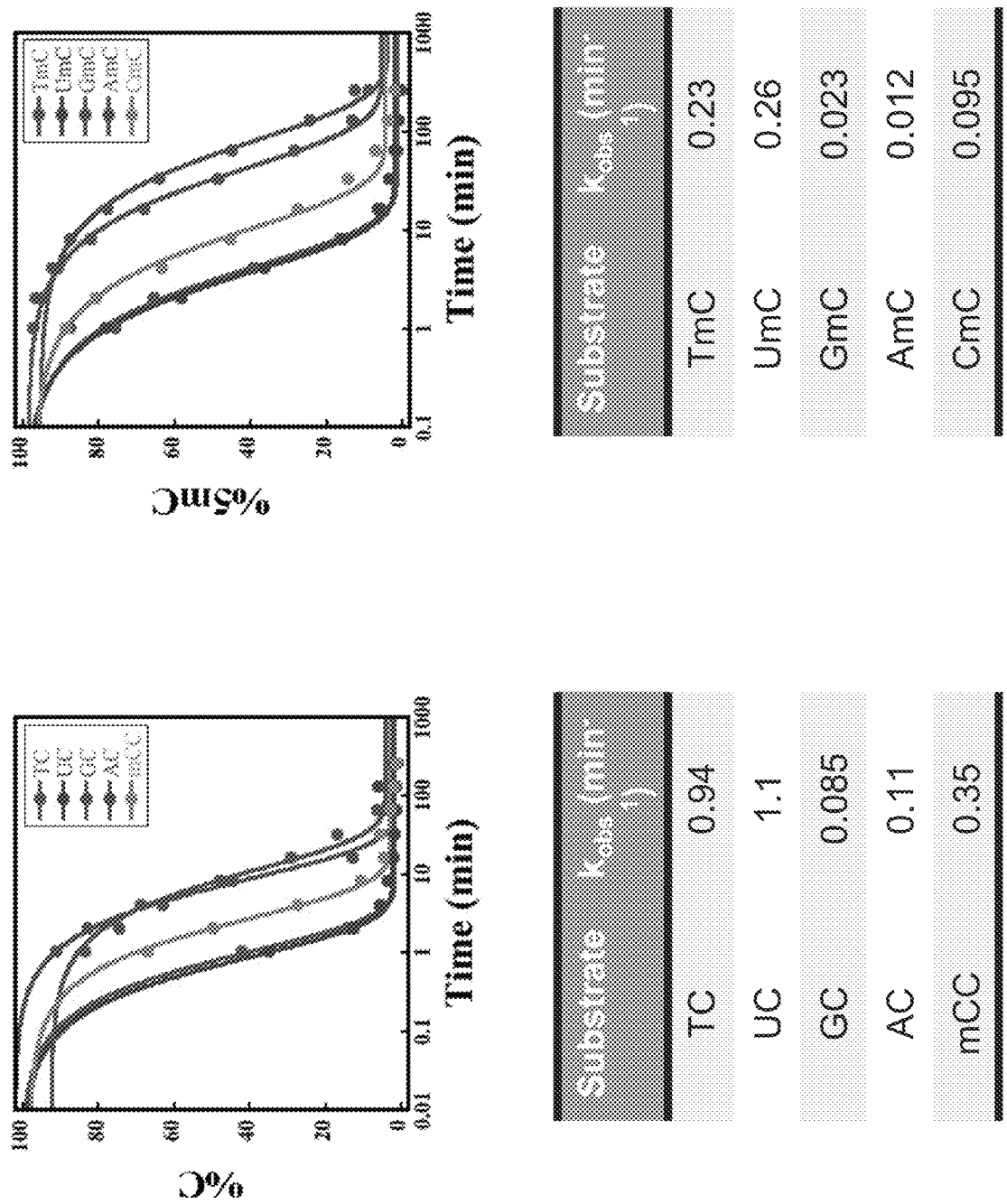
FIG. 15 shows that APOBEC3A can substantially completely deaminate both C and 5 mC.
Figure 16:
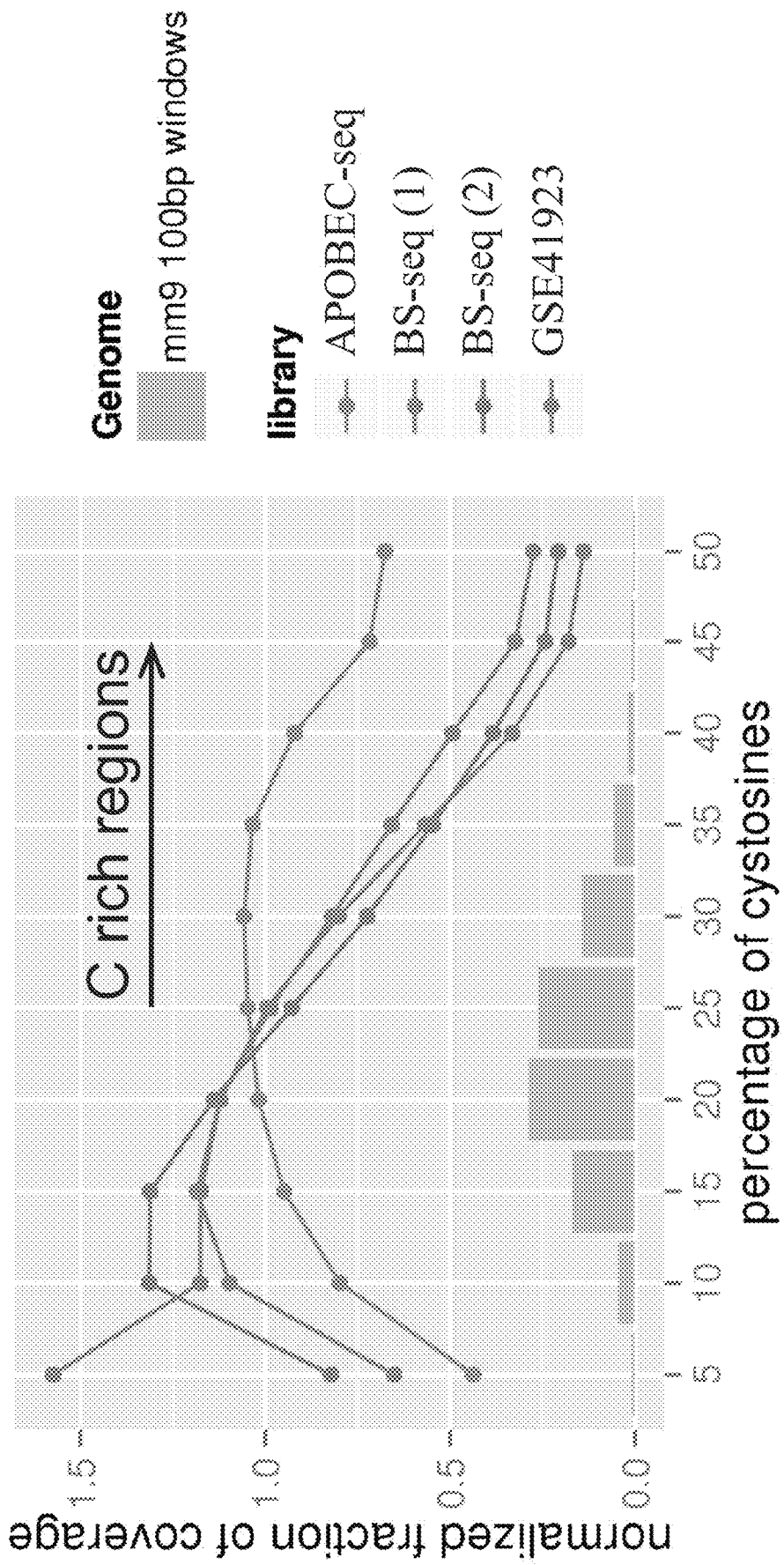
FIG. 16 shows that low sequence bias of deaminase-Seq includes accurate representation of cytosine in cytosine rich fragments such as CpG islands. Cytosine in CpG islands are substantially depleted using bisulfite sequencing.
Figure 17:
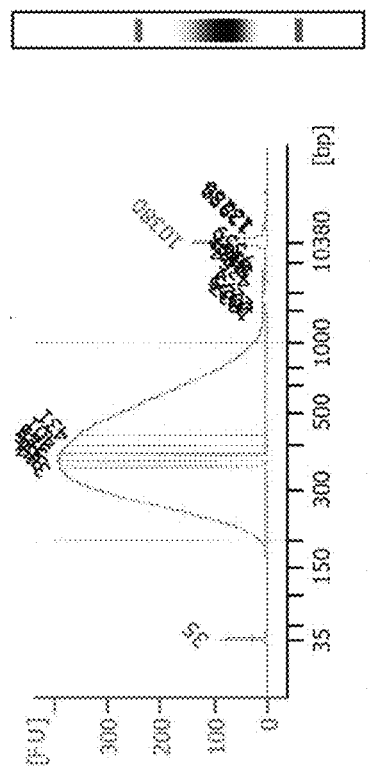
FIG. 17 shows that the lack of fragmentation using Deaminase-Seq correlates with a low nucleic acid starting concentration for detecting the position of modified bases in the nucleic acid. For example, Ing of a genomic DNA library is sufficient for detecting or mapping normal and modified cytosine.
Figure 18:
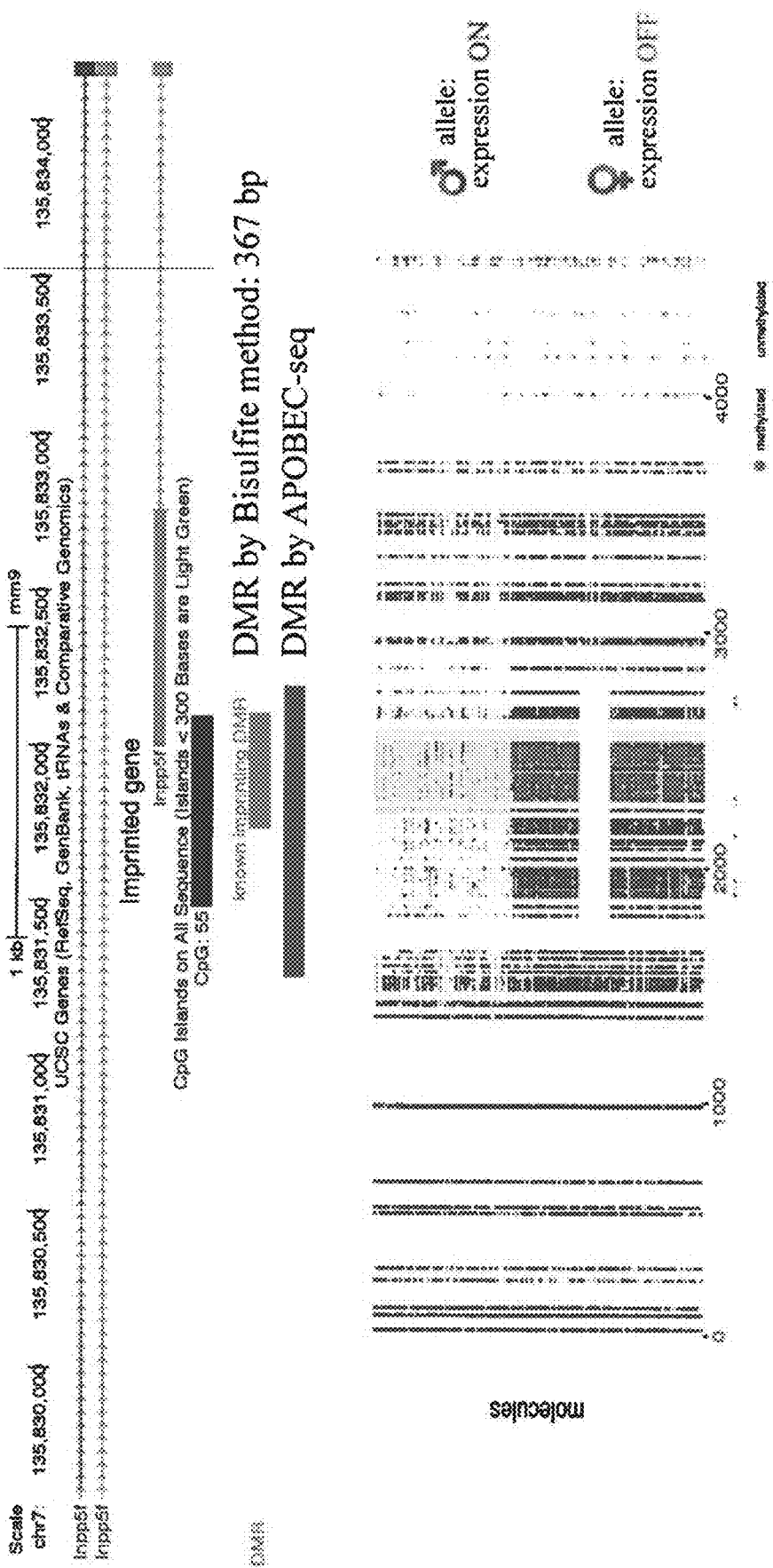
FIG. 18 shows a second example of methylome phasing (also see FIG. 10 and FIG. 11A-11B) using embodiments of the methods described herein where the results of methylome phasing using Deaminase-Seq (SMRT® sequencing, (Pacific Biosciences, Menlo Park, Calif.)) of an imprinted gene. The region of imprinting identified by bisulfite sequencing is relatively short while a region of greater than twice the length is identified using Deaminase-Seq. Each red dots on the sequence map correspond to a modified cytosine.

The reaction products were resolved on a 1.8% agarose gel. The results are shown in FIG. 14.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications (e.g. epigenetic analysis) those skilled in the art will recognize that its usefulness is not limited thereto and that the present invention can be beneficially utilized in any number of environments and implementations where it is desirable to examine DNA. Accordingly, the claims set forth below should be construed in view of the full breadth and spirit of the invention as disclosed herein.

What is claimed is:

1. A protein comprising SEQ ID NO:2 and having methyl cytosine dioxygenase activity.

2. The protein of claim 1, wherein the protein is a fusion protein.

3. The protein of claim 1, wherein the fusion protein has an N-terminal affinity binding domain.

4. A kit comprising a protein of claim 1 contained in one vessel, and optionally a cytidine deaminase in a second vessel and instructions for use.

5. The kit of claim 4, wherein the concentration of the protein in the one vessel provides a concentration of 0.001-100 micrograms in a reagent or in a reaction mix.

6. The kit of claim 5, wherein the one vessel further comprises 0.001-100 units of a glucosyltransferase in the reagent or the reaction mix.

7. A composition comprising the protein of claim 1, wherein the composition further comprises a nucleic acid, wherein the nucleic acid comprises:
   a. guanine (G), adenine (A), thymine (T), uracil (U), cytosine (C);
   b. G, A, T, U, carboxycytosine and no C; or
   c. G, A, T, U, no C and a modified hydroxymethylcytosine wherein the modification is capable of blocking oxidation by a methylcytosine dioxygenase.

* * * * *

UNITED STATES PATENT AND TRADEMARK OFFICE
CERTIFICATE OF CORRECTION

PATENT NO. : 11,124,825 B2  
APPLICATION NO. : 16/217819  
DATED : September 21, 2021  
INVENTOR(S) : Romualdas Vaisvila et al.

Page 1 of 1

It is certified that error appears in the above-identified patent and that said Letters Patent is hereby corrected as shown below:

On the Title Page

Please replace item (72) inventors:
"Romualdas Vaisvila, Ipswich, MA (US); Zhiyi Sun, Gloucester, MA (US); Shengxi Guan, Ipswich, MA (US); Lana Saleh, Hamilton, MA (US); Laurence Ettwiller, Ipswich, MA (US); Theodore B. Davis, Boxford, MA (US)"

With:
--Romualdas Vaisvila, Ipswich, MA (US); Zhiyi Sun, Gloucester, MA (US); Shengxi Guan, Ipswich, MA (US); Lana Saleh, Hamilton, MA (US); Laurence Ettwiller, Ipswich, MA (US); Theodore B. Davis, Boxford, MA (US); Thomas C. Evans, Jr., Ipswich, MA (US)--

Signed and Sealed this  
Twenty-second Day of July, 2025

Coke Morgan Stewart  
*Acting Director of the United States Patent and Trademark Office*